United States Patent
Brown et al.

(10) Patent No.: US 12,011,422 B2
(45) Date of Patent: Jun. 18, 2024

(54) SYNTHETIC ANTIBACTERIAL COMPOUNDS AND USES THEREOF

(71) Applicant: McMaster University, Hamilton (CA)

(72) Inventors: Eric Brown, Oakville (CA); Omar M Elhalfawy, Regina (CA); Nick Jentsch, Fenton, MO (US); Xiong Zhang, Tianjin (CN); Jakob Magolan, Grimsby (CA)

(73) Assignee: McMaster University, Ontario (CA)

( * ) Notice: Subject to any disclaimer, the term of this patent is extended or adjusted under 35 U.S.C. 154(b) by 0 days.

(21) Appl. No.: 17/826,770

(22) Filed: May 27, 2022

(65) Prior Publication Data

US 2022/0401384 A1    Dec. 22, 2022

Related U.S. Application Data

(60) Provisional application No. 63/194,725, filed on May 28, 2021.

(51) Int. Cl.

| | |
|---|---|
| A61K 31/055 | (2006.01) |
| A61K 31/05 | (2006.01) |
| A61K 31/11 | (2006.01) |
| A61K 31/121 | (2006.01) |
| A61K 31/341 | (2006.01) |
| A61K 31/381 | (2006.01) |
| A61K 31/42 | (2006.01) |
| A61K 31/4418 | (2006.01) |
| A61K 31/47 | (2006.01) |
| A61K 31/505 | (2006.01) |
| A61K 38/12 | (2006.01) |
| A61P 31/04 | (2006.01) |
| C07C 39/19 | (2006.01) |
| C07C 43/275 | (2006.01) |
| C07C 49/78 | (2006.01) |
| C07C 205/18 | (2006.01) |
| C07D 213/30 | (2006.01) |
| C07D 215/14 | (2006.01) |
| C07D 239/26 | (2006.01) |
| C07D 239/42 | (2006.01) |
| C07D 261/08 | (2006.01) |
| C07D 307/48 | (2006.01) |
| C07D 333/38 | (2006.01) |

(52) U.S. Cl.
CPC ............ *A61K 31/055* (2013.01); *A61K 31/05* (2013.01); *A61K 31/11* (2013.01); *A61K 31/121* (2013.01); *A61K 31/341* (2013.01); *A61K 31/381* (2013.01); *A61K 31/42* (2013.01); *A61K 31/4418* (2013.01); *A61K 31/47* (2013.01); *A61K 31/505* (2013.01); *A61K 38/12* (2013.01); *A61P 31/04* (2018.01); *C07C 39/19* (2013.01); *C07C 43/275* (2013.01); *C07C 49/78* (2013.01); *C07C 205/18* (2013.01); *C07D 213/30* (2013.01); *C07D 215/14* (2013.01); *C07D 239/26* (2013.01); *C07D 239/42* (2013.01); *C07D 261/08* (2013.01); *C07D 307/48* (2013.01); *C07D 333/38* (2013.01)

(58) Field of Classification Search
None
See application file for complete search history.

(56) References Cited

U.S. PATENT DOCUMENTS

2022/0017482 A1*   1/2022   Brown ............... A61K 31/4184

FOREIGN PATENT DOCUMENTS

FR   10186602200 B1   11/2017

OTHER PUBLICATIONS

Masagalli et al., Synthesis of Moracin C and Its Derivatives with a 2-arylbenzofuran Motif and Evaluation of Their PCSK9 Inhibitory Effects in HepG2 Cells, 2021, Molecules, 26, 1327, pp. 1-11 (Year: 2021).*
You et al., Pharmacokinetic Properties of Moracin C in Mice, 2021, Planta Med, 87, 642-651 (Year: 2021).*
Kim et al., Chalcomoracin and Moracin C, New Inhibitors of *Staphylococcus aureus* Enoyl-Acyl Carrier Protein Reductase From Morus alba, 2012, Biol. Pharm. Bull., 35(5) 791-795 (Year: 2012).*
2-[(2E)-3,7-Dimethyl-2,6-octadien-1-yl]-5-(6-hydroxy-2-benzofuranyl)-1,3-benzenediol. National Center for Biotechnology Information. https://pubchem.ncbi.nlm.nih.gov/compound/14237687 (translated and untranslated versions of the KR), 2022.
Machine Translation of KR 10186602200—Cosmetic composition for skin whitening containing Campylotropis hirtella extract with inhibitory activity of tyrosinase and melanin formation, 2022.

* cited by examiner

*Primary Examiner* — Kristin A Vajda
(74) *Attorney, Agent, or Firm* — Gowling WLG (Canada) LLP

(57) ABSTRACT

Provided herein are novel synthetic compounds having the structure of formula (1),

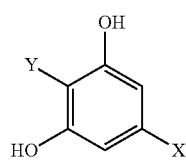

Formula (1)

wherein X is a substituted or unsubstituted aromatic or heteroaromatic mono- or polycyclic ring system; and Y is substituted or unsubstituted $C^5$-$C^{10}$ alkyl or alkenyl group, or a pharmaceutically acceptable salt thereof. Also provided are pharmaceutical compositions. The compounds and pharmaceutical compositions are useful for inhibiting growth of a bacterium.

17 Claims, 1 Drawing Sheet

| Compound ID | Structure | E. coli X-axis Analogue 0-32 ug/mL; Y-axis Colistin 0-0.5 ug/mL |
|---|---|---|
| MLEB-1917 | 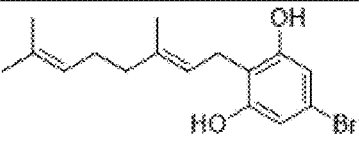 |  |
| MLEB-1850 | 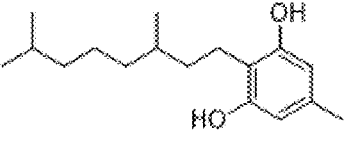 |  |

SYNTHETIC ANTIBACTERIAL COMPOUNDS AND USES THEREOF

FIELD OF THE INVENTION

The present application provides synthetic antibacterial compounds and methods of use thereof. The compositions and methods are effective against bacteria, including bacteria that are persisters.

BACKGROUND OF THE INVENTION

Over the past 20 years, there has been an explosion in the prevalence of antibiotic resistant bacterial infections, both in the hospital and in the general community. Notably, the ESKAPE pathogens (*Enterococcus faecium, Staphylococcus aureus, Klebsiella pneumoniae, Acinetobacter baumannii, Pseudomonas aeruginosa*, and *Enterobacter* species) are responsible for a substantial percentage of nosocomial infections and present serious therapeutic challenges for physicians. These multi-drug resistant infections increase morbidity and mortality, and often lead to increased usage of ineffective or last resort antibiotics.

Exacerbating the problem can be the presence of non-growing, dormant persister (i.e., non-planktonic) subpopulations of bacteria, which can also exhibit high levels of resistance to current treatments. Persisters may play a role in some chronic and relapsing bacterial infections such as osteomyelitis.

As conventional antibiotics are not effective in the treatment of such bacterial infections, the development of novel antibacterial compounds active against drug-resistant bacterial infections, including those arising from persisters, remains an unmet need.

SUMMARY OF THE INVENTION

The invention provides compounds having the structure of formula (1):

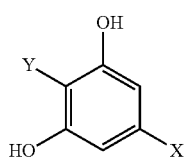

Formula 1

The invention further provides compositions comprising (i) an effective amount of a compound of formula (1) or a pharmaceutically acceptable salt thereof; and (ii) a pharmaceutically acceptable carrier or vehicle.

The invention still further provides methods for inhibiting growth of a bacterium, comprising contacting the bacterium with an effective amount of a compound of formula (1) or a pharmaceutically acceptable salt thereof.

The invention further provides methods for treating or preventing a bacterial infection, comprising administering to a subject in need thereof an effective amount of a compound of formula (1) or a pharmaceutically acceptable salt thereof.

BRIEF DESCRIPTION OF THE FIGURE

FIG. 1 illustrates the checkerboard analysis of compounds in accordance with an aspect of the invention.

DETAILED DESCRIPTION OF THE INVENTION

The compounds of the invention are useful for inhibiting growth of a bacterium or for treating or preventing a bacterial infection.

Also provided herein are compositions comprising (i) an effective amount of a compound of the invention and (ii) a pharmaceutically acceptable carrier or vehicle (each composition being a "composition of the invention"). The compositions of the invention are useful for inhibiting growth of a bacterium or for treating or preventing a bacterial infection.

Further provided herein are methods for inhibiting growth of a bacterium, comprising contacting the bacterium with an effective amount of a compound of the invention.

Still further provided herein are methods for treating or preventing a bacterial infection, comprising administering to a subject in need thereof an effective amount of a compound of the invention.

Each of the aforementioned methods is a "method of the invention".

In some embodiments, the methods of the invention are useful for inhibiting growth of a bacterium, wherein the bacterium is a persister bacterium. In some embodiments, the methods of the invention are useful for treating a bacterial infection by a bacterium, wherein the bacterium is a persister bacterium. In some embodiments, the bacterium is alive, but dormant or metabolically inactive. In some embodiments, the bacterium is a drug-resistant or a multi-drug-resistant bacterium. In some embodiments, the bacterium is *Staphylococcus aureus* USA300.

Definitions

The term "about" when immediately preceding a numerical value means±0% to 10% of the numerical value, ±0% to 10%, ±0% to 9%, ±0% to 8%, ±0% to 7%, ±0% to 6%, ±0% to 5%, ±0% to 4%, ±0% to 3%, ±0% to 2%, ±0% to 1%, ±0% to less than 1%, or any other value or range of values therein. For example, "about 40" means±0% to 10% of 40 (i.e., from 36 to 44).

In embodiments referencing an "additional," "other", "another" or "second" component, such as an, additional, other, another, or second antibacterial agent, the second component is non-identical to the first component.

The term "bacterial infection" as used herein refers to an infection by a bacterium. In some embodiments, the bacterial infection is a pulmonary, lung, otic, oral, nasal, sinus, ophthalmic, intraocular, dermal, cardiovascular, kidney, urinary, gastrointestinal, rectal, vaginal, neurological or systemic infection.

The term "subject" as used herein means a human, a non-human primate, a horse, a cow, a sheep, a goat, a pig, a dog, a cat, a rabbit, a hamster, a guinea pig, a rat, a mouse, a duck, a goose, a chicken or a turkey.

The term "pharmaceutically acceptable salt" includes: an acid addition salt of a basic active agent, including a basic compound of the invention or another antibacterial agent; and a base addition salt of an acidic active agent, including an acidic compound of the invention or another antibacterial agent.

Basic active agents that form an acid addition salt include, for example, those comprising a proton-accepting moiety, e.g., a nitrogen atom of a pyridino, pyrimidino, pyrazino, imidazolino, benzimidazolino, pyrazolino, oxazolino, thiazolino, piperazino or morpholino group, or a sulfur atom of a thioether group. Illustrative inorganic acids that form acid addition salts with basic active agents include hydrochloric, hydrobromic, sulfuric, nitric and phosphoric acids, as well as acidic metal salts such as sodium monohydrogen orthophosphate and potassium hydrogen sulfate. Illustrative organic acids that form acid addition salts with basic active agents include mono-, di-and tricarboxylic acids. Illustrative of such organic acids are, for example, acetic, trifluoroacetic, propionic, glycolic, lactic, pyruvic, malonic, succinic, glutaric, fumaric, malic, oxalic, tartaric, citric, ascorbic, maleic, hydroxymaleic, benzoic, hydroxybenzoic, phenylacetic, cinnamic, mandelic, salicylic, 2-phenoxybenzoic, isethionic, p-toluenesulfonic acid and other sulfonic acids such as methanesulfonic acid, ethanesulfonic acid and 2-hydroxyethanesulfonic acid. Mono- or poly-acid salts can be formed, and such salts can exist in either a hydrated, solvated or substantially anhydrous form.

Acidic active agents that form a base addition salt include, for example, compounds comprising a proton-donating moioety, e.g., a carboxylic acid, a phenolic hydroxyl group, an NH-imidazolyl group, NH-indolyl group, or NH-benzimidazolyl group. Illustrative inorganic bases that form base addition salts with acidic acid agents include lithium, sodium, potassium, calcium, magnesium or barium hydroxides, carbonates and bicarbonates, as well as ammonia. Illustrative organic bases that form base addition salts with acidic active agents include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Illustrative organic bases are isopropylamine, diethylamine, ethanolamine, trimethylamine, dicyclohexylamine, choline, and caffeine. (See, for example, S. M. Berge, et al, "Pharmaceutical Salts," J. Pharm. Sci. 1977, 66, 1-19).

The formation of pharmaceutically acceptable salts is achieved using standard techniques well known to those skilled in the art. For example, an active agent having a proton-accepting moiety can be treated with an acid and an acid agent having a proton-donating moietyh can be treated with a base, in each case in a suitable solvent, and the resultant pharmaceutically acceptable salt can be isolated by filtration, extraction or any other suitable method.

As used herein, the term "effective amount" means an amount that is effective for inhibiting growth of a bacterium or for treating or preventing a bacterial infection. Where a composition of the invention comprises another antibacterial agent, the effective amount of the compound of the invention and antibacterial agent is the total amount of the compound of the invention and antibacterial agent that is effective for inhibiting growth of a bacterium or for treating or preventing a bacterial infection. Where a method of the invention further comprises administering another antibacterial agent, the effective amount of the compound of the invention and antibacterial agent is the total amount of the compound of the invention and antibacterial agent that is effective for inhibiting growth of a bacterium or for treating or preventing a bacterial infection.

The term "MIC" as used herein, refers to the "minimal inhibitory concentration" of an antibacterial agent.

The term "MRSA", as used herein, refers to methicillin-resistant *Staphylococcus aureus*.

The term "MSSA", as used herein, refers to methicillin-sensitive *Staphylococcus aureus*.

Compounds

Compounds in accordance with invention have the following general chemical formula (1):

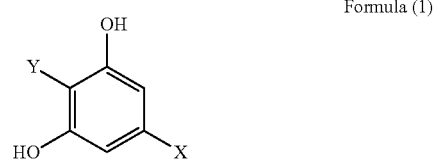

Formula (1)

wherein X is a substituted or unsubstituted aromatic or heteroaromatic mono- or polycyclic ring system; and
Y is substituted or unsubstituted $C^5$-$C^{10}$ alkyl or alkenyl group,
with the proviso that the compound is not 2-[3,5-dihydroxy-4-(3,7-dimethyl-2,6-octadienyl)phenyl]-6-hydroxybenzofuran.

X may be an aromatic mono-cyclic ring such as a benzyl ring, as well as a polycyclic ring. Polycyclic aromatic rings include naphthalene, biphenyl, phenanthrene, anthracene, fluoren, phenalene, tetracene and the like.

Heteroaromatic mono- or polycyclic nitrogen-containing rings include, but are not limited to, pyrrole, pyrazole, pyridine, pyrimdine, pyrazine, pyridazine, imidazole, purine, benzimidazole, benzopyrrole, dibenzopyrrole, indazole, indole, isoindole, indolizine, quinoline, quinazoline, isoquinoline, quinoxaline, cinnoline, phthalazine and triazine.

Heteroaromatic mono- or polycyclic oxygen-containing rings include, but are not limited to, furan, benzofuran, dibenzofuran, isobenzofuran, coumarin and xanthone.

Heteroaromatic mono- or polycyclic sulfur-containing rings include, but are not limited to, thiophene, thiepine, benzothiophene, benzo[c]thiophene, dibenzothiophene, 2,2'-bithiophene, thienothiophene and thionine.

Heteroaromatic rings including 2 different heteroatoms include, for example, thiazole, benzothiazole, oxazole, benzoxazole, isoxazole, benzisoxazole, oxadiazole, dioxazole and thiazopine.

In one embodiment, X is a monocyclic, bicyclic or other polycyclic, aromatic or heteroaromatic ring.

The aromatic or polycyclic ring may be substituted at one or more positions on the ring or rings. Substituents (R) may include one or more substituents referred to as "$R^1$", "$R^2$", "$R^3$", etc., including, but not limited to, hydroxyl, halogen (e.g. F, Br, Cl, I), amino, nitro, nitrile, carboxyl, thiol, sulfinyl, sulfonamide and sulfinamide.

Substituents may also include an alkyl, alkenyl, alkoxy, alkanal, alkanone, acetyl, alkoxycarbonyl, amine, amide, sulfoxide or sulfonyl comprising one to ten carbon atoms, preferably comprising one to eight carbon atoms, two carbon atoms, three carbon atoms, 4 carbon atoms, 5 carbon atoms, 6 carbon atoms or 7 carbon atoms, optionally, substituted with one or more R groups. With respect to carbon-containing substituents, the term "lower" indicates 1-5 carbon atoms.

In embodiments, X is a an aromatic mono-cyclic ring such as a benzyl ring, furan, thiophene, pyrrole, pyridine, pyrazole, pyridine, pyrimdine, pyrazine, pyridazine, thiazole, oxazole, isoxazole and thiazopine. The mono-cyclic ring may be unsubstituted. Alternatively, the mono-cyclic ring is substituted with one or more of halogen, hydroxyl, nitrile, a lower alkyl such as a methyl, ethyl, propyl, butyl or pentyl, substituted alkyl, e.g. with a halogen such as trifluoromethyl or other substituent, amino, nitro and thiol.

Exemplary X substituents include, but are not limited to, 2-chlorophenyl, 2,6-difluoro-phenyl, 3,5-bis(trifluoromethyl)phenyl, 2-chloropyridin-3-yl, 2-fluoro-5-(trifluoromethyl)-phenyl, 2-fluoro-4-formylphenyl, 3,5-dimethylisoxazol-4-yl, 4-methoxyphenyl, 3-hydroxyphenyl, pyrimidin-5-yl and quinolin-3-yl.

Y is an unbranched or branched $C^5$-$C^{12}$ alkyl chain or a corresponding unsaturated carbon chain. Thus, Y may be pentyl, hexyl, heptyl octyl, nonyl, decyl, unidecyl or dodecyl, or Y may incorporate 1 or more double bonds. Y may incorporate 1 or more lower alkyl branches, e.g. $C^1$-$C^5$ alkyl groups. In one embodiment, Y is an octyl group. In another embodiment, Y is a 2,6-octadienyl group. In another embodiment, Y includes a lower alkyl branch at its 3- and 7-positions. In a preferred embodiment, Y is 3,7-dimethyl-2,6-octa-dienyl.

General Synthesis Methods

The Compounds of formula (1) can be synthesized according to the general reaction scheme shown in Scheme 1.

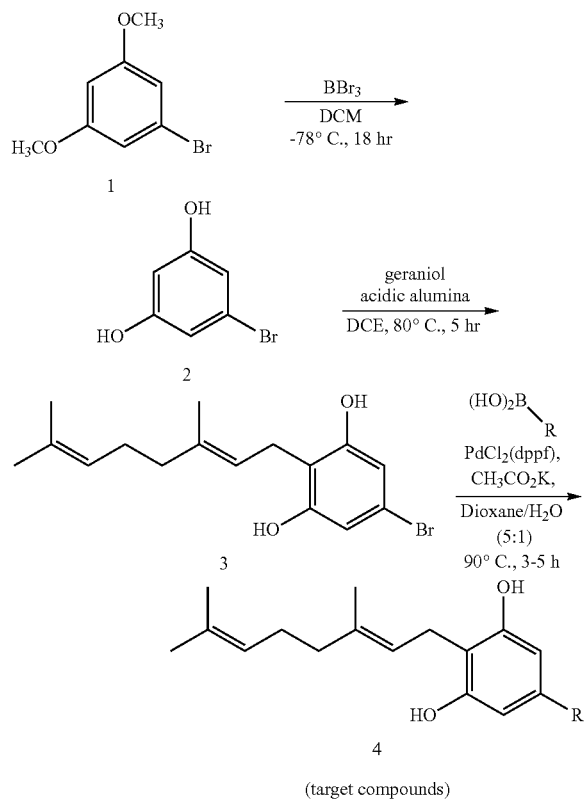

Compounds of formula (1) can be synthesized using established synthesis protocols. For example, in one embodiment, the present compounds can be synthesized according to Scheme 1. A suitably substituted 3,5-dimethoxybenzene compound, e.g. substituted at the 1-position with a reactive group (R) such as a halogen, nitrile or other reactive group, is first deprotected to yield the corresponding benzene-1,3-diol (2; R=Br) which is then condensed with an allylic alcohol in the presence of a suitable Lewis Acid catalyst, e.g., acidic alumina or $BF_3$-etherate, to provide the allylated compound 3 intermediate. Cross-coupling of Compound 3 with an aryl or heteroaryl boronic acid or boronate ester (or alternatively with a corresponding aryl or heteroaryl stannane or tin reagent under Stille conditions) in the presence of a palladium catalyst, e.g., $Pd(Ph_3)_4$, $PdCl_2dppf$, etc. provides the desired Compound 4.

Bacteria

Provided herein are methods for inhibiting growth of a bacterium, comprising contacting the bacterium with an effective amount of a compound of the invention.

Also provided herein are methods for treating or preventing a bacterial infection, comprising administering to a subject in need thereof an effective amount of a compound of the invention.

In some embodiments, the bacterium is a Gram-negative bacterium. In some embodiments, the bacterium is a Gram-positive bacterium.

In some embodiments, the bacterium is a sphere-shaped bacterium, a rod-shaped bacterium, a spiral-shaped bacterium, a filamentous bacterium, a pleomorphic bacterium or a rectangular bacterium. In some embodiments, the bacterium is a spherical-shaped (coccus), a rod-shaped (*bacillus*), or a spiral-shaped bacterium. In some embodiments, the bacterium is a Gram-positive rod-shaped bacterium. In some embodiments, the bacterium is a Gram-positive spherical-shaped bacterium. In some embodiments, the bacterium is a Gram-negative rod-shaped bacterium. In some embodiments, the bacterium is a Gram-negative spherical-shaped bacterium.

In some embodiments, the bacterium is an aerobic bacterium. In some embodiments, the aerobic bacterium is an obligate aerobe. In some embodiments, the bacterium is an anaerobic bacterium. In some embodiments, the anaerobic bacterium is an obligate anaerobe, an aerotolerant anaerobe, or a facultative anaerobe.

In some embodiments, the bacterium is a drug-resistant or multidrug-resistant (MDR) bacterium. In some embodiments, the bacterium is carbapenem-resistant, fluoroquinoline-resistant, vancomycin-resistant, methicillin-resistant, clarithromycin-resistant, ampicillin-resistant, tetracycline-resistant, cephalosporin-resistant, or combinations thereof. In some embodiments, the bacterium is carbapenem-resistant, fluoroquinoline-resistant, vancomycin-resistant, methicillin-resistant, cephalosporin-resistant, or combinations thereof. In some embodiments, the bacterium is methicillin-resistant. In some embodiments, the bacterium is carbapenem-resistant. In some embodiments, the carbapenem-resistant bacterium is an extended spectrum beta-lactamase (ESBL)-producing bacterium. ESBL-producing bacteria are Gram-negative bacteria that produce beta-lactamase enzymes that have the ability to break down commonly used antibiotics such as carbapenems and cephalosporins. In some embodiments, the carbapenem-resistant bacterium is a New Delhi metallo-beta-lactamase 1 (NDM-1) producing bacterium.

In some embodiments, the bacterium is a Gram-negative bacterium. Gram-negative bacteria are characterized by their cell envelopes, which are composed of a thin peptidoglycan cell wall sandwiched between an inner cytoplasmic cell membrane and a bacterial outer membrane composed of phospholipids and lipopolysaccharides which face the external environment.

In some embodiments, the Gram-negative bacterium is a species of Acetic acid bacteria, *Acidaminococcus, Anaerobiospirillum, Arcobacter, Bacteroides*, Bacteroidetes, *Bdellovibrio, Brachyspira, Campylobacter, Christensenella*, Cyanobacteria, *Cytophaga, Dialister, Enterobacter*, Enterobacteriaceae, Enterobacteriales, *Escherichia, Flavobacterium, Haemophilus, Helicobacter, Legionella, Megamonas, Megasphaera, Meiothermus, Moraxella, Pectinatus, Pelosinus, Propionispora*, Proteobacteria, *Pseudomonas, Salmonella, Samsonia*, Selenomonadales, *Shigella, Shimwellia, Spirochaeta*, Spirochaetaceae, *Sporomusa, Stenotrophomonas*, Thorselliaceae, Vampirococcus, *Verminephrobacter, Vitreoscilla, Wolbachia*, Yersiniaceae, or *Zymophilus*.

In some embodiments, the Gram-negative bacterium is a species of *Acinetobacter, Campylobacter, Enterobacter, Escherichia, Haemophilus, Helicobacter, Klebsiella, Neisseria, Pseudomonas, Salmonella*, or *Shigella*.

In some embodiments, the Gram-negative bacterium is *Acinetobacter baumannii, Agrobacterium tumefaciens, Akkermansia muciniphila, Anaerobiospirillum, Anaerolinea thermolimosa, Anaerolinea* thermophile, *Arcobacter skirrowii, Armatimonas rosea, Azotobacter salinestris, Bacteroides fragilis, Bacteroides thetaiotaomicron, Bacteroides ureolyticus, Bartonella japonica, Bartonella koehlerae, Bartonella taylorii, Bradyrhizobium japonicum, Caldilinea aerophila, Cardiobacterium hominis*, Chaperone-Usher fimbriae, *Chthonomonas calidirosea, Coxiella burnetii, Dehalogenimonas lykanthroporepellens, Desulfurobacterium atlanticum, Devosia pacifica, Devosia psychrophila, Devosia soli, Devosia subaequoris, Devosia submarina, Devosia yakushimensis, Dictyoglomus thermophilum, Dinoroseobacter shibae, Enterobacter cloacae, Enterobacter cowanii*, Enterobacteriales, *Escherichia coli, Escherichia fergusonii, Escherichia hermannii, Fimbriimonas ginsengisoli, Flavobacterium akiainvivens, Francisella novicida, Fusobacterium necrophorum, Fusobacterium nucleatum, Fusobacterium polymorphum, Gluconacetobacter diazotrophicus, Haemophilus felis, Haemophilus haemolyticus, Haemophilus influenza, Haemophilus pittmaniae, Helicobacter typhlonius, Kingella kingae, Klebsiella pneumoniae, Kluyvera ascorbata, Kluyvera cryocrescens, Kozakia baliensis, Legionella clemsonensis, Legionella pneumophila, Leptonema illini, Leptotrichia buccalis, Levilinea saccharolytica, Luteimonas aestuarii, Luteimonas* aquatic, *Luteimonas composti, Luteimonas lutimaris, Luteimonas* marina, *Luteimonas mephitis, Luteimonas vadosa, Meiothermus timidus, Methylobacterium fujisawaense*, Morax-Axenfeld diplobacilli, *Moraxella bovis, Moraxella osloensis, Morganella morganii, Mycoplasma spumans, Neisseria cinerea, Neisseria gonorrhoeae, Neisseria meningitides, Neisseria polysaccharea, Neisseria sicca, Nitrosomonas eutropha, Nitrosomonas halophile, Nitrosomonas stercoris, Pedobacter heparinus, Proteus mirabilis, Proteus penneri, Pseudomonas aeruginosa, Pseudomonas luteola, Pseudomonas teessidea, Pseudoxanthomonas broegbernensis, Pseudoxanthomonas japonensis, Rickettsia rickettsia, Riemerella anatipestifer, Salinibacter ruber, Salmonella bongori, Salmonella enterica, Selenomonas noxia, Serratia marcescens, Solobacterium moorei, Sorangium cellulosum, Sphaerotilus natans, Sphingomonas gei, Stenotrophomonas nitritireducens, Thermotoga neapolitana, Vibrio adaptatus, Vibrio azasii, Vibrio campbellii, Vibrio cholera, Victivallis vadensis*, or *Yersinia pestis*.

In some embodiments, the Gram-negative bacterium is *Klebsiella pneumoniae, Acinetobacter baumanii, Pseudomonas aeruginosa, Enterobacter cloacae, Haemophilus influenzae, Helicobacter pylori, Neisseria gonorrhoeae, Yersinia pestis*, or *Escherichia coli*.

In some embodiments, the bacterium is a Gram-positive bacterium. Gram-positive bacteria are characterized by the presence of a thick peptidoglycan cell wall, but lack the outer membrane found in a Gram-negative bacterium.

In some embodiments, the Gram-positive bacterium is a species of Actinobacteria, *Actinomyces, Arcanobacterium*, Bacillales, *Bacillus, Bavariicoccus, Brachybacterium*, Carnobacteriaceae, *Clostridium*, Cnuibacter, Coriobacteriia, *Corynebacterium, Enterococcus, Janibacter*, Lactobacillales, Listeriaceae, *Nocardia, Pasteuria, Pilibacter, Roseburia, Sarcina, Solibacillus, Sporosarcina, Staphylococcus, Streptococcus*, or *Tepidibacter*.

In some embodiments, the Gram-positive bacterium is *Actinomyces bovis, Actinomyces georgiae, Actinomyces gerencseriae, Actinomyces israelii, Actinomyces neuii, Actinomyces radicidentis, Actinomyces viscosus, Alicyclobacillus acidocaldarius, Alicyclobacillus acidoterrestris, Alicyclobacillus aeris, Alicyclobacillus contaminans, Alicyclobacillus cycloheptanicus, Alicyclobacillus dauci, Alicyclobacillus disulfidooxidans, Alicyclobacillus fastidiosus, Alicyclobacillus ferrooxydans, Alicyclobacillus kakegawensis, Alicyclobacillus macrosporangiidus, Alicyclobacillus sacchari, Alicyclobacillus shizuokensis, Alicyclobacillus tolerans, Bacillus mojavensis, Bacillus subtilis, Bacillus weihenstephanensis, Brachybacterium alimentarium, Brachybacterium aquaticum, Brachybacterium conglomeratum, Brachybacterium faecium, Brachybacterium fresconis, Brachybacterium ginsengisoli, Brachybacterium horti, Brachybacterium huguangmaarense, Brachybacterium massiliense, Brachybacterium muris, Brachybacterium nesterenkovii, Brachybacterium paraconglomeratum, Brachybacterium phenoliresistens, Brachybacterium rhamnosum, Brachybacterium tyrofermentans, Clostridium acetobutylicum, Clostridium aerotolerans, Clostridium argentinense, Clostridium autoethanogenum, Clostridium baratii, Clostridium beijerinckii, Clostridium bifermentans, Clostridium botulinum, Clostridium butyricum, Clostridium cadaveris, Clostridium cellobioparum, Clostridium cellulolyticum, Clostridium cellulovorans, Clostridium chauvoei, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paradoxum, Clostridium paraputrificum, Clostridium pasteurianum, Clostridium perfringens, Clostridium phytofermentans, Clostridium pilforme, Clostridium ragsdalei, Clostridium ramosum, Clostridium saccharobutylicum, Clostridium saccharoperbutylacetonicum, Clostridium scatologenes, Clostridium septicum, Clostridium sordellii, Clostridium sporogenes, Clostridium stercorarium, Clostridium sticklandii, Clostridium straminisolvens, Clostridium tertium, Clostridium tetani, Clostridium thermosaccharolyticum, Clostridium tyrobutyricum, Clostridium uliginosum, Corynebacterium amycolatum, Corynebacterium bovis, Corynebacterium diphtheria, Corynebacterium efficiens, Corynebacterium glutamicum, Corynebacterium granulosum, Corynebacterium jeikeium, Corynebacterium macginleyi, Corynebacterium minutissimum, Corynebacterium renale, Corynebacterium ulcerans, Cutibacterium acnes, Deinococcus marmoris, Desulfitobacterium dehalogenans, Enterococcus faecium, Enterococcus*

*faecalis, Fervidobacterium changbaicum, Fervidobacterium gondwanense, Fervidobacterium islandicum, Georgenia ruanii, Microbispora coralline, Nocardia asteroids, Nocardia brasiliensis, Nocardia farcinica, Nocardia ignorata, Rathayibacter toxicus, Rhodococcus equi, Rothia dentocariosa, Sporosarcina aquimarina, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus lutrae, Staphylococcus muscae, Staphylococcus nepalensis, Staphylococcus pettenkoferi, Staphylococcus pseudintermedius, Staphylococcus saprophyticus, Staphylococcus schleiferi, Staphylococcus succinus, Staphylococcus warneri, Staphylococcus xylosus, Streptococcus agalactiae, Streptococcus anginosus, Streptococcus canis, Streptococcus downei, Streptococcus equi, Streptococcus bovis, Streptococcus gordonii, Streptococcus iniae, Streptococcus lactarius, Streptococcus mitis, Streptococcus mutans, Streptococcus oralis, Streptococcus parasanguinis, Streptococcus peroris, Streptococcus pneumoniae, Streptococcus pyogenes, Streptococcus ratti, Streptococcus salivarius, Streptococcus sanguinis, Streptococcus sobrinus, Streptococcus suis, Streptococcus thermophiles, Streptococcus tigurinus, Streptococcus uberis, Streptococcus vestibularis, Syntrophomonas curvata, Syntrophomonas palmitatica, Syntrophomonas sapovorans, Syntrophomonas wolfei, Syntrophomonas zehnderi,* or *Viridans* streptococci.

In some embodiments, the Gram-positive bacterium is *Enterococcus faecium, Staphylococcus aureus,* or *Streptococcus pneumoniae*. In some embodiments, the bacterium is *Staphylococcus aureus*. In some embodiments, the *Staphylococcus aureus* is methicillin-resistant *Staphylococcus aureus* or methicillin-sensitive *Staphylococcus aureus*. In some embodiments, the *Staphylococcus aureus* is vancomycin-resistant *Staphylococcus aureus* or vancomycin-intermediate *Staphylococcus aureus*. In some embodiments, the *Staphylococcus aureus* is vancomycin-resistant *Staphylococcus aureus*.

In some embodiments, the bacterium is present on a substrate. In some embodiments, the bacterium is present on a substrate's painted surface. In some embodiments, the substrate is glass, metal, plastic, latex, ceramic, cement, wood, grout, stone or biological tissue. In some embodiments, the bacterium is present on or in a surgical instrument. In some embodiments, the bacterium is present on or in a catheter, an implant, a stent or a surgical mesh. In some embodiments, the bacterium is present in a biofilm.

Persister Bacteria

In some embodiments, the bacterium is a persister bacterium. In some embodiments, the bacterial infection is caused by a persister bacterium. In some embodiments, the persister bacterium is a Gram-negative bacterium. In some embodiments, the persister bacterium is a Gram-positive bacterium. In some embodiments, the persister bacterium is a drug-resistant or a multidrug-resistant bacterium.

In some embodiments, the bacterium is alive, but dormant or metabolically inactive. In some embodiments, the bacterium is non-growing or a member of a dormant subpopulation that becomes tolerant to antibiotic treatment or reaches this state without undergoing genetic change. In some embodiments, the bacterium is non-planktonic. In some embodiments, the bacterium does not undergo a cellular activity that a conventional antibiotic can inhibit. In some embodiments, the bacterium is conventional-antibiotic-tolerant. In some embodiments, a bacterial infection, particularly a bacterial infection by a persister bacterium, is a chronic bacterial infection. In some embodiments, a bacterial infection, particularly a bacterial infection by a persister bacterium, is a relapsing bacterial infection. In some embodiments, the chronic or relapsing bacterial infection, particularly by a persister bacterium, is osteomyelitis, endocarditis or an infection of an implanted device. In some embodiments, the persister bacterium is present in a biofilm.

In some embodiments, the persister bacterium is a species of *Enterococcus, Staphylococcus, Streptococcus, Haemophilus, Helicobacter, Campylobacter, Salmonella, Shigella, Neisseria, Klebsiella, Acinetobacter, Pseudomonas,* Enterobacteriaceae, or *Enterobacter.*

In some embodiments, the persister bacterium is *Escherichia coli, Lactobacillus acidophilus, Gardnerella vaginalis, Enterococcus faecium, Staphylococcus aureus, Staphylococcus epidermidis, Streptococcus pneumoniae, Klebsiella pneumoniae, Acinetobacter baumannii, Pseudomonas aeruginosa, Haemophilus influenzae, Helicobacter pylori, Neisseria gonorrhoeae, Yersiniapestis,* or *Enterobacter cloacae*. In some embodiments, the persister bacterium is *Staphylococcus aureus*. In some embodiments, the *Staphylococcus aureus* is *Staphylococcus aureus* strain USA300. In some embodiments, the persister bacterium is *Staphylococcus epidermidis*. In some embodiments, the *Staphylococcus epidermidis* is *Staphylococcus epidermidis* strain RP62a. Illustrative examples of persister bacteria are described in Waters et al., *PLoS Pathog.* 2016 December; 12(12): e1006012; Conlon et al., *Nat Microbiol* 1, 16051, doi: 10.1038/nmicrobiol.2016.51 (2016); Conlon et al., *Bioessays* 36, 991-996 (2014); Lewis, *Nat Rev Microbiol.* 2007 January; 5(1):48-56; Shapiro et al., *Journal ofMedicalMicrobiology* (2011), 60, 950-960; Fisher et al., *Nat Rev Microbiol.* 2017 August; 15(8): 453-464; Miyaue et al., (2018) *Front. Microbiol.* 9:1396.

In some embodiments, the persister bacterium is a drug-resistant or a multidrug-resistant bacterium. In some embodiments, the drug-resistant or multidrug-resistant persister bacterium is a Gram-positive bacterium. In some embodiments, the drug-resistant or multidrug-resistant persister bacterium is a Gram-negative bacterium.

In various embodiments, the persister bacterium exhibits one or more resistance phenotypes disclosed herein (e.g., fluoroquinolone-resistance, methicillin-resistance, and/or carbapenem-resistance), including any other resistance phenotype known in the art. In some embodiments, where the persister bacterium is *Staphylococcus aureus,* the *Staphylococcus aureus* is methicillin-resistant *Staphylococcus aureus* (MRSA) or methicillin-sensitive *Staphylococcus aureus* (MSSA). In some embodiments, the persister bacterium is methicillin-resistant *Staphylococcus aureus*. In some embodiments, the persister bacterium is vancomycin-resistant *Staphylococcus aureus* or vancomycin-intermediate *Staphylococcus aureus*.

In some embodiments, the compounds of the invention are bacteriostatic. In other embodiments, the compounds of the invention are bacteriocidal. In some embodiments, the compounds of the invention kill greater than 99% of a bacterial population or a bacterial colony within 18-24 h. In some embodiments, the compounds of the invention have a (minimum bacteriocidal concentration (MBC)):(minimum inhibitory concentration (MIC)) ratio that is greater than 4:1.

In some embodiments, the compositions of the invention are bacteriostatic. In some embodiments, the compositions are bacteriocidal. In some embodiments, the compositions of the invention kill greater than 99% of of a bacterial population or a bacterial colony within 18-24 h. In some embodiments, the compositions of the invention have a (minimum bacteriocidal concentration (MBC)):(minimum inhibitory concentration (MIC)) ratio that is greater than 4:1.

Other Antibacterial Agents

In some embodiments, the compositions of the invention further comprise another antibacterial agent.

In some embodiments, the methods of the invention further comprise administering another antibacterial agent.

In some embodiments, the other antibacterial agent is a macrolide, an aminoglycoside, a tetracycline, a peptide (e.g., glycopeptide, lipopeptide, lipoglycopeptide, cationic peptide, or the like) a penicillin, a cephalosporin, a quinolone, a fluoroquinolone, a rifampin, or a pharmaceutically acceptable salt thereof.

In some embodiments, the other antibacterial agent is an aminoglycoside. In some embodiments, the other antibacterial agent is apramycin, gentamicin, kanamycin, neomycin, paromycin, spectinomycin, a combination thereof, or a pharmaceutically acceptable salt thereof.

In some embodiments, the other antibacterial agent is a penicillin or a pharmaceutically acceptable salt thereof. In some embodiments, the other antibacterial agent is ampicillin, amoxicillin, cloxacillin, piperacillin, oxacillin, a combination thereof, or a pharmaceutically acceptable salt thereof.

In some embodiments, the other antibacterial agent is a cephalosporin or a pharmaceutically acceptable salt thereof. In some embodiments, the other antibacterial agent is ceftriaxone, cefoperazone, cefepime, a combination thereof, or a pharmaceutically acceptable salt thereof.

In some embodiments, the other antibacterial agent is a quinolone, fluoroquinolone, or a pharmaceutically acceptable salt thereof. In some embodiments, the other antibacterial agent is ciprofloxacin, besifloxacin, enoxacin, nalidixic acid, norfloxacin, levofloxacin, moxifloxacin, pefloxin, a combination thereof, or a pharmaceutically acceptable salt thereof.

In some embodiments, the other antibacterial agent is a peptide. In some embodiments, the peptide is bacitracin, dalbvancin, daptomycin, oritivancin, teicoplanin, televancin, guavanin 2, or vancomycin. In some embodiments, the peptide is a cationic peptide. In some embodiments, the other antibacterial agent is a cationic peptide. In some embodiments, the cationic peptide is polymyxin B, polymyxin B nonapeptide, or Colistin. In some embodiments, the cationic peptide comprises or consists of the sequence RWRWRW—NH$_2$ (SEQ ID NO:1) (also referred to as "MP196", Wenzel et al., *PNAS*, 2014, 111 (14) E1409-E1418); RWWRWWRRWWRR (SEQ ID NO:2) (also referred to as "WR12", Deslouches et al., *Antimicrobial-Agents and Chemotherapy*, 2013, 57 (6) 2511-2512); RRWVRRVRRWVRRVVRVVRRWVRR (SEQ ID NO:3) (also referred to as "WLBU2", Deslouches et al., *Antimicrobial Agents and Chemotherapy*, 2005, 49 (1) 316-322); or GAKYAKIIYNYLKKIANALW (SEQ ID NO:4) (also referred to as "GW-A2", Li et al., *PLoS ONE*, 2017, 12 (7) e0182057); or is a pharmaceutically acceptable salt thereof.

In some embodiments, where the bacterial infection is by a Gram-negative bacterium, the other agent is an outer membrane-damaging agent. In some embodiments, the outer membrane-damaging agent is a cationic peptide. Non-limiting examples of cationic peptides useful as outer membrane-damaging agents, include, but are not limited to polymyxin B, polymyxin B nonapeptide, and Colistin.

In some embodiments, the other antibacterial agent is Amikacin, Apramycin, Gentamicin, Kanamycin, Neomycin, Tobramycin, Paromomycin, Streptomycin, Spectinomycin, Ertapenem, Doripenem, Imipenem/Cilastatin, Meropenem, Cefadroxil, Cefazolin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Lipopeptide, Daptomycin, Azithromycin, Clarithromycin, Dirithromycin, Erythromycin, Roxithromycin, Troleandomycin, Telithromycin, Spiramycin, Aztreonam, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Bacitracin, Colistin, Polymyxin B, Besifloxacin, Ciprofloxacin, Enoxacin, Gatifloxacin, Gemifloxacin, Levofloxacin, Lomefloxacin, Moxifloxacin, Nalidixic acid, Norfloxacin, Ofloxacin, Pefloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfonamidochrysoidine, Demeclocycline, Doxycycline, Minocycline, Oxytetracycline, Tetracycline, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, Trimethoprim, Clofazimine, Dapsone, Capreomycin, Cycloserine, Ethambutol, Ethionamide, Isoniazid, Pyrazinamide, Rifampicin, Rifabutin, Rifapentine, Fosmidomycin, Pefloxin, Novobiocin, Delafloxacin, or Eravacycline, or a pharmaceutically acceptable salt thereof.

In some embodiments, where the compositions of the invention further comprise another antibacterial agent, the ratio of a compound of the invention to the other antibacterial agent is about 50:1, about 45:1, about 40:1, about 35:1, about 30:1, about 25:1, about 20:1, about 15:1, about 10:1, about 5:1, about 1:1, about 1:5, about 1:10, about 1:15, about 1:20, about 1:25, about 1:30, about 1:35, about 1:40, about 1:45, or about 1:50, including all ranges and values therebetween, by moles or by weight.

In some embodiments, where the methods of the invention further comprise administering another antibacterial agent, the ratio of a compound of the invention to the other antibacterial agent is about 50:1, about 45:1, about 40:1, about 35:1, about 30:1, about 25:1, about 20:1, about 15:1, about 10:1, about 5:1, about 1:1, about 1:5, about 1:10, about 1:15, about 1:20, about 1:25, about 1:30, about 1:35, about 1:40, about 1:45, or about 1:50, including all ranges and values therebetween, by moles or by weight.

In some embodiments, the compositions of the invention comprise another antibacterial agent in an amount that is less than an amount that is lethal to the bacterium. In some embodiments, the compositions of the invention comprise another antibacterial agent in an amount or above the amount that is lethal to the bacterium. In some embodiments, the compositions of the invention comprise another antibacterial agent in an amount that is less than an amount that is bacteriostatic. In some embodiments, the compositions of the invention comprise another antibacterial agent in an amount or above the amount that is bacteriostatic In some embodiments, the methods of the invention comprise administering another antibacterial agent in an amount that is less than an amount that is lethal to the bacterium. In some embodiments, the methods of the invention comprise administering another antibacterial agent in an amount or above the amount that is lethal to the bacterium. In some embodiments, the methods of the invention comprise administering another antibacterial agent in an amount that is less than an amount that is bacteriostatic. In some embodiments, the methods of the invention comprise administering another antibacterial agent in an amount or above the amount that is bacteriostatic.

In some embodiments, a compound of the invention and another antibacterial agent are synergistic. In some embodiments, administration of a compound of the invention and another antibacterial agent results in an increased inhibition of bacterial growth of about 5% to about 100%, e.g., about 5%, about 10%, about 15%, about 20%, about 25%, about 30%, about 35%, about 40%, about 45%, 50%, about 55%, about 60%, about 65%, about 70%, about 75%, about 80%, about 85%, about 90%, about 95%, or 100%, including all ranges and values therebetween, compared to inhibition of bacterial growth resulting from administration of a compound of the invention in the absence of another antibacterial agent or administration of the other antibacterial agent in the absence of the compound of the invention.

In some embodiments, administration of a compound of the invention and another antibacterial agent to a subject results in at least a 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 40-fold, 50-fold, 75-fold, 100-fold, 125-fold, 150-fold, 175-fold or 200-fold increase in activity (e.g., inhibition of bacterial growth) compared to administration of a compound of the invention in the absence of another antibacterial agent or administration of the other antibacterial agent in the absence of the compound of the invention.

In some embodiments, the presence of another antibacterial agent decreases the MIC of a compound of the invention by at least 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 40-fold, 50-fold, 75-fold, 100-fold, 125-fold, 150-fold, 175-fold or 200-fold compared to the MIC of a compound of the invention in the absence of another antibacterial agent or of the other antibacterial agent in the absence of a compound of the invention.

In some embodiments, a compound of the invention and another antibacterial agent are synergistic. In some embodiments, a fractional inhibitory concentration (FIC) index calculation (shown below) is used to show synergy of a compound of the invention and another antibacterial agent. In some embodiments, the FIC for each of the compound of the invention and other antibacterial agent is calculated as the concentration of the compound of the invention or the other antibacterial agent in the presence of the other that results in less than 10% bacterial growth, divided by the MIC for the compound of the invention or the other antibacterial agent, as the case may be, as shown here: $FIC_{compound\ of\ the\ invention}$=[compound of the invention]/$MIC_{compound\ of\ the\ invention}$, where [compound of the invention] is the lowest inhibitory concentration of the compound of the invention in the presence of another inhibitory agent.

$FIC_{other\ antibacterial\ agent}$=[other antibacterial agent]/$MIC_{other\ antibacterial\ agent}$, where [other antibacterial agent] is the lowest inhibitory concentration of the other antibacterial agent in the presence of a compound of the invention.

The FIC index (FICI) is the sum of the $FIC_{compound\ of\ the\ invention}$ and $FIC_{other\ antibacterial\ agent}$. Drug-Drug interactions having an FICI of less than or equal to 0.5 are deemed synergistic. In some embodiments, a compound of the invention and another antibacterial agent have a FICI of about 0.5, about 0.4, about 0.3, about 0.2, about 0.1 or about 0. In some embodiments, a compound of the invention and another antibacterial agent have a FICI ranging from about 0.5 to about 0.4, from about 0.4 to about 0.3, from about 0.3 to about 0.2, from about 0.2 to about 0.1 or from about 0.1 to about 0.

Methods of Administration and Compositions of the Invention

The compounds of the invention can be administered to a subject, or used in a variety of forms depending on the selected route of administration, as will be understood by those skilled in the art.

In vivo application of the compounds of the invention and compositions of the invention can be accomplished by any suitable method and technique presently or prospectively known to those skilled in the art. For example, the compounds of the invention can be formulated in a physiologically- or pharmaceutically-acceptable form and administered by any suitable route known in the art including, for example, oral and parenteral routes of administration. As used herein, the term parenteral includes subcutaneous, intradermal, intravenous, intramuscular, intraperitoneal, and intrasternal administration, such as by injection. Administration of the compounds of the invention or compositions of the invention can comprise a single administration, or a plurality of administrations at continuous or distinct intervals.

The compositions of the invention comprise (i) an effective amount of a compound of the invention and (ii) a pharmaceutically acceptable carrier or vehicle.

In some embodiments, a composition of the invention comprises a compound of the invention in an amount of about 0.001 wt % to about 75 wt %, about 0.005 wt % to about 61.5 wt %, about 0.01 wt % to about 50 wt %, about 2 wt % to about 35 wt %, or about 2 wt % to about 21 wt % of the composition. In some embodiments, a composition of the invention comprises a compound of the invention in an amount of about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, or about 75%, by weight of the composition, or an amount ranging from and to these values.

Pharmaceutically acceptable carriers or vehicles include without limitation any adjuvant, excipient, glidant, sweetening agent, diluent, preservative, dye/colorant, flavor enhancer, surfactant, wetting agent, dispersing agent, suspending agent, stabilizer, isotonic agent, solvent, or emulsifier.

In some embodiments, suitable pharmaceutically acceptable carriers include, but are not limited to, inert solid fillers or diluents and sterile aqueous or organic solutions. Pharmaceutically acceptable carriers are well known to those skilled in the art and include, but are not limited to, aqueous and non-aqueous solutions. Pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate. Aqueous carriers suitable for use in the present application include, but are not limited to, water, ethanol, alcoholic/aqueous solutions, glycerol, emulsions or suspensions, including saline and buffered media.

The compositions of the invention can comprise soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In a further embodiment, the compositions of the invention can comprise biodegradable polymers useful for achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Solid carriers suitable for use as pharmaceutically acceptable carriers or vehicles include, but are not limited to, inactive substances such as lactose, starch, glucose, methylcellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material.

Conventional procedures and ingredients for the selection and preparation of compositions of the invention are described, for example, in *Remington's Pharmaceutical Sciences* (2000-20th edition) and in The United States Pharmacopeia: The National Formulary (USP 24 NF19) published in 1999. In general, compositions of the present disclosure can be used in the form in which they are available and administered to subjects. Such forms, include, for example in the form of their pharmaceutically acceptable salts, in the form of fine particles of the zwitterionic form and in an injectable or infusable suspensions. The compositions of the invention can be solid, semi-solid, and liquid dosage forms, such as tablets, pills, powders, liquid solutions or suspension, suppositories, injectable and infusible solutions, and sprays. The preferred form depends on the intended mode of administration and therapeutic application. As described herein, the compositions of the invention can comprise conventional pharmaceutically-acceptable carriers and diluents which are known to those skilled in the art. To provide for the administration of such dosages for the desired therapeutic treatment, compositions of the invention can advantageously comprise between about 0.1% and 100% by weight of the total of one or more of a compound of the invention based on the weight of the total composition including carrier or diluent.

In some embodiments, the compositions of the invention can be administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump, intraocular and transdermal) administration and the compound(s) formulated accordingly. In some embodiments, the compositions of the invention are administered to the subject orally. In some embodiments, the compositions of the invention are administered parenterally. In some embodiments, the parental administration is intravenous administration.

In some embodiments, a compound of the invention and another antibacterial agent are administered via different modes of administration. For example, in some embodiments, a compound of the invention is administered parenterally and the other antibacterial agent is administered orally. In some embodiments, compound of the invention is administered orally and the other antibacterial agent is administered parenterally.

When administered orally, the compositions of the invention can be orally administered, for example, with an inert diluent or with an assimilable edible carrier, or they can be enclosed in hard or soft shell gelatin capsules, or compressed into tablets, or incorporated directly with the food of a diet. For oral administration, the compositions of the invention can be incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In some embodiments, timed-release compositions can be, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of lipids, such as cholesterol, stearylamine or phosphatidylcholines.

Compositions of the invention suitable for injectable use can include sterile aqueous solutions or dispersions and sterile powders for the extemporaneous preparation of sterile injectable solutions or dispersions. In some embodiments, the compositions are sterile and fluid to the extent that easy syringability exists.

In some embodiments, parenteral administration can be by continuous infusion over a selected period of time. Solutions suitable for parenteral administration can be prepared by known methods by a person skilled in the art. For example, the compositions of the invention can be prepared in water optionally mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations can contain a preservative to prevent the growth of microorganisms.

It is also possible to freeze-dry the compositions of the invention and use the lyophilizate obtained, for example, for the preparation of products for injection Compositions of the invention useful for nasal administration can be conveniently formulated as aerosols, drops, gels or powders. Aerosol formulations typically comprise a solution or fine suspension of the active substance in a physiologically acceptable aqueous or non-aqueous solvent and are can be prepared in single or multidose quantities in sterile form in a sealed container, which take the form of a cartridge or refill for use with an atomising device. Alternatively, the sealed container can be a unitary dispensing device such as a single dose nasal inhaler or an aerosol dispenser fitted with a metering valve which is intended for disposal after use. Where the dosage form comprises an aerosol dispenser, it can contain a propellant which is, for example, a compressed gas such as compressed air or an organic propellant such as fluorochlorohydrocarbon. In some embodiments, the aerosol dosage forms can take the form of a pump-atomizer.

Compositions of the invention suitable for buccal or sublingual administration can include tablets, lozenges, and pastilles, wherein the active ingredient is formulated with a carrier such as sugar, acacia, tragacanth, gelatin and/or glycerine. Compositions of the invention useful for rectal administration can conveniently be in the form of suppositories containing a conventional suppository base such as cocoa butter.

In some embodiments, the compositions of the invention can be administered as a topical composition, such as a solution, gel, cream, lotion, liquid suspension, aerosol, nebulized spray, ointment, drops or patch.

In some embodiments, the compositions of the invention are suitable for administration intraocularly. In some embodiments, the compositions of the invention are useful as an ophthalmic topical solution or gel, or is for topical, subconjunctival, periocular, retrobulbar, sub-tenon, intracameral, intravitreal, intraocular, subretinal, juxtascleral or suprachoroidal administration.

Thus, in some embodiments provided herein, the compositions of the invention are useful for treating an ophthalmic infection is provided. In some embodiments, the composition contains an (i) effective amount a compound of the present disclosure and (ii) a pharmaceutical carrier or vehicle suitable for ocular administration. In some embodiments, compositions of the invention suitable for ocular administration can be presented as discrete dosage forms, such as drops or sprays each containing a predetermined amount of the active ingredient(s) in a solution, or a suspension in an aqueous or non-aqueous liquid, an oil-in-water emulsion, or a water-in-oil liquid emulsion. Other administration forms can include intraocular injection, intravitreal injection, topically, or through the use of a drug eluting device, microcapsule, implant, or microfluidic device. In some embodiments, the compounds as provided herein can be administered with a carrier or excipient that increases the intraocular penetrance of the compound such as an oil and water emulsion with colloid particles having an oily core surrounded by an interfacial film. The compositions of the invention can be administered to the eye via topical, subconjunctival, periocular, retrobulbar, subtenon, intracameral, intravitreal, intraocular, subretinal, juxtascleral and suprachoroidal administration.

In some embodiments, eye drops can be prepared by dissolving the active ingredient(s) in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives can include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some embodiments, the methods of the invention and compositions of the invention are useful to treat a pulmonary, lung, otic, oral, nasal, sinus, ophthalmic, intraocular, dermal, cardiovascular, kidney, urinary, gastrointestinal, rectal, vaginal, neurological or systemic infection.

Further provided herein is a compound of the invention for use in therapy. In some embodiments, provided herein is a compound of the invention for use in a method of treating a bacterial infection. In further embodiments, provided herein is a compound of the invention for the manufacture of a medicament for treating a bacterial infection.

A compound of the invention and another antibacterial agent can be administered concurrently or sequentially. Where administered concurrently, the compound of the invention and other antibacterial agent can be administered together in the same composition of the invention or each can be administered in a separate composition. Where administered sequentially, the compound of the invention and other antibacterial agent can be administered separately by the same mode of administration, or they can be administered separately by different modes of administration. For example, the compound of invention can be administered by injection and the other antibacterial agent can be administered orally. In some embodiments, the compound of the invention can be administered orally and the other antibacterial agent agent can be administered by injection. In some embodiments, both the compound of the invention and the other antibacterial agent can be administered orally, topically or by injection. Where a compound of the invention and the other antibacterial agent administered sequentially, the compound of the invention can be administered before or after administration of the other antibacterial agent.

In some embodiments, a compound of the invention and the other antibacterial agent can be present in a composition of the invention, or each can be present in a separate composition. In some embodiments, a compound of the invention and another antibacterial agent are not present in the same composition.

In some embodiments, where the compositions of the invention comprise another antibacterial agent, the compositions can be administered or used according to treatment protocol that is known for other antibacterial agents in the treatment in bacterial infections.

In some embodiments, the compounds of the invention or compositions of the invention can be administered or used as soon as practicable after a subject is exposed to a bacterium. In some embodiments, the compounds of the invention or compositions of the invention can be administered or used until treatment of the bacterial infection is achieved or until the bacterial infection is completely resolved, for example, until complete elimination of the bacterium is achieved, or until the number of bacteria has been reduced to the point where the subject's defenses are no longer overwhelmed and can kill any remaining bacteria.

The dosage of the compounds of the invention or compositions of the invention can vary depending on many factors such as the pharmacodynamic properties thereof, the mode of administration, the age, health and weight of the subject, the nature and extent of the symptoms, the frequency of the treatment and the type of concurrent treatment, if any, and the clearance rate in the subject to be treated. One of skill in the art can determine the appropriate dosage based on the above factors. In some embodiments, the compositions are administered initially in a suitable dosage that may be adjusted as required, depending on the clinical response.

In some embodiments, a dosage of a compound of the invention or another antibacterial agent ranges from about 1 mg to about 50 mg. In some embodiments, a dosage of a compound of the invention is about 1 mg, about 2 mg, about 3 mg, about 4 mg, about 5 mg, about 6 mg, about 7 mg, about 8 mg, about 9 mg, about 10 mg, 11 mg, about 12 mg, about 13 mg, about 14 mg, about 15 mg, about 16 mg, about 17 mg, about 18 mg, about 19 mg, about 20 mg, 21 mg, about 22 mg, about 23 mg, about 24 mg, about 25 mg, about 26 mg, about 27 mg, about 28 mg, about 29 mg, about 30 mg, 31 mg, about 32 mg, about 33 mg, about 34 mg, about 35 mg, about 36 mg, about 37 mg, about 38 mg, about 39 mg, about 40 mg, 41 mg, about 42 mg, about 43 mg, about 44 mg, about 45 mg, about 46 mg, about 47 mg, about 48 mg, about 49 mg, about 50 mg, or an amount ranging from and to any of these values.

In some embodiments, a dosage of a compound of the invention or another antibacterial agent ranges from about 50 mg to about 900 mg. In some embodiments, a dosage of a compound of the invention is about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, or an amount ranging from and to any of these values.

In some embodiments, a dosage of a compound of the invention ranges from about 0.001 mg/kg to about 100 mg/kg, where "mg" refers to the amount of the compound and "kg" refers to the body weight of a subject. In some embodiments, a dosage of a compound of the invention ranges from about 0.001 mg/kg to about 75 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight.

In some embodiments, the dosage is a once-daily dose. In some embodiments, the dosage is a twice-daily dose. In some embodiments, the dosage is a thrice-daily dose. In some embodiments, the dosage is a four-times-daily dose. In some embodiments, the dosage is continuous.

In some embodiments, the dosage, or effective amount, of the other antibacterial agent can be equal to or less than the dosage of such agents where used alone. Such dosages are known to or readily determined by those skilled in the art.

EXAMPLES

The following examples illustrate the scope of the application. Specific elements of the examples are for descriptive purposes only and are not intended to limit the scope of the invention. Those skilled in the art could develop equivalent methods and utilize comparable materials that are within the scope of the application.

Example 1: Synthesis of Compounds of Formula (1)

Synthesis of 5-bromobenzene-1,3-diol-To a 500 mL 2-neck roundbottom flask was added 1-bromo-3,5-dimethoxybenzene (20 g, 92.1 mmol) and dichloromethane (50 mL). This solution was cooled to −78° C. before dropwise addition of boron tribromide (26.6 mL, 276.4 mmol) in dichloromethane (50 mL) via pressure-equalizing addition funnel over 60 minutes. The reaction was warmed slowly to ambient temperature then stirred overnight for a total of 18 hours. The reaction was cooled to 0° C. then quenched with dropwise addition of methanol (30 mL) via pressure equalizing addition funnel over 60 minutes. The solution was diluted with water (50 mL) and the resultant white slurry was vacuum filtered through a Celite plug. The filtrate was collected and the phases split. The aqueous phase was extracted with ethyl acetate (three 3-mL portions). The combined organic phase was dried over magnesium sulfate, gravity filtered, and concentrated to afford an orange-red oil (24 g). The residue was split into four equal portions and purified over a 40 g silica column eluted with hexanes-ethyl acetate. Product rich fractions were pooled and evaporated to afford 2 as a white solid (13.6 g, 78%). 1H NMR (700 MHz, CDCl3): δ 6.60 (d, J=2.2 Hz, 1H), 6.30 (s, 1H), 6.08 (s, 1H).

Synthesis of (E)-5-bromo-2-(3, 7-dimethylocta-2,6-dien-1-yl)benzene-1, 3-diol-To a 250 mL roundbottom flask was added 5-bromobenzene-1,3-diol (3.5 g, 18.5 mmol), geraniol (2.1 mL, 12.3 mmol), alumina (24.6 g, 2 g/mmol loading) and dichloroethane (50 mL). The reaction was stirred and heated to 80° C. for 5 hours. The reaction was cooled to ambient temperature and filtered through a Celite plug. The filtrate was collected and concentrated in vacuo. The residue was chromatographed over a Gold 40 g Teledyne silica column eluted with hexanes-ethyl acetate. Product rich fractions were pooled and evaporated to afford 3 as a yellow oil (1.7 g, 42%). 1H NMR (700 MHz, CDCl3): δ 6.58 (s, 1H), 5.41 (s, 1H), 5.23 (t, J=7.0 Hz, 1H), 5.04 (t, J=6.2 Hz, 1H), 3.37 (d, J=7.1 Hz, 1H), 2.11 (q, J=7.3, 6.7 Hz, 2H), 1.80 (s, 2H), 1.68 (s, 2H), 1.59 (s, 2H).

General Procedure for Suzuki Coupling Reactions-To a 40 mL vial with a septum cap was added (E)-5-bromo-2-(3,7-dimethylocta-2,6-dien-1-yl)benzene-1,3-diol (50 mg, 0.15 mmol), potassium acetate (4.0 eq), the desired boronic acid (1.5 eq), (1,1'-bis(diphenylphosphino)ferrocene)-dichloropalladium (10 mol %) and a mixture of 1,4-dioxane and water (5:1, 2.0 mL). The vial was equipped with a magnetic stirring bar, sealed and the mixture degassed with argon for 25 minutes. The reaction was then heated to 90° C. for 12-18 hours. The reaction was then cooled to ambient temperature, then quenched with water (1.0 mL) and extracted with ethyl acetate (three 2-mL portions). The organic layer was washed with brine (5.0 mL), dried over MgSO$_4$, gravity filtered, and concentrated in vacuo. The crude residue was chromatographed over a 12 g SiO$_2$ column eluted with hexanes-ethyl acetate. Product rich fractions were pooled and evaporated to afford the desired bi-aryl coupling product.

1H NMR characterization data for selected compounds synthesized according to the above methods follows:

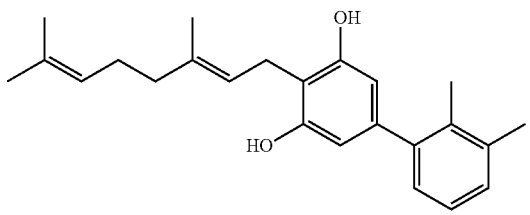 [SMILES: CC(C)=CCC/C(C)=C/Cc1c(O)cc(-c2cccc(C)c2C)cc1O]

$^1$H NMR (700 MHz, CDCl$_3$) δ 7.14 (dd, J=7.5, 1.8 Hz, 1H), 7.10 (t, J=7.5 Hz, 1H), 7.05 (dd, J=7.5, 1.6 Hz, 1H), 6.35 (s, 2H), 5.34 (tq, J=7.2, 1.4 Hz, 1H), 5.15 (s, 2H), 5.07 (tt, J=7.0, 1.4 Hz, 1H), 3.47 (d, J=7.1 Hz, 2H), 2.32 (s, 3H), 2.17 (s, 3H), 2.15-2.11 (m, 2H), 2.12-2.07 (m, 2H), 1.84 (s, 3H), 1.68 (s, 3H), 1.60 (s, 3H).

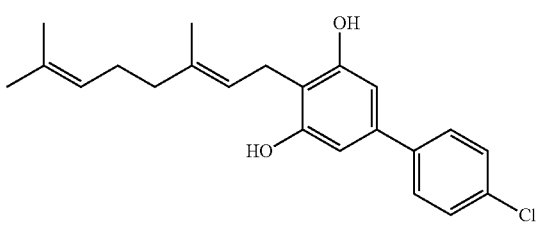 [SMILES: CC(C)=CCC/C(C)=C/Cc1c(O)cc(-c2ccc(Cl)cc2)cc1O]

$^1$H NMR (700 MHz, CDCl$_3$) δ 7.46-7.42 (m, 2H), 7.38-7.34 (m, 2H), 6.61 (s, 2H), 5.30 (t, J=7.2 Hz, 1H), 5.25 (s, 2H), 5.06 (t, J=6.5 Hz, 1H), 3.46 (d, J=7.1 Hz, 2H), 2.14-2.11 (m, 2H), 2.10-2.07 (m, 2H), 1.84 (s, 3H), 1.69 (s, 3H), 1.60 (s, 3H).

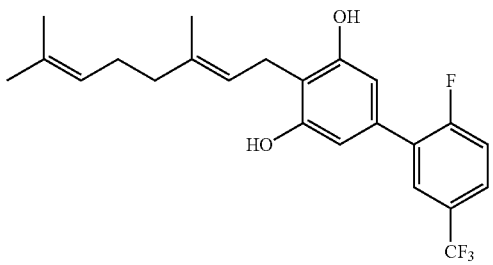 [SMILES: CC(C)=CCC/C(C)=C/Cc1c(O)cc(-c2cc(C(F)(F)F)ccc2F)cc1O]

$^1$H NMR (700 MHz, CDCl$_3$) δ 7.69 (dd, J=7.0, 2.4 Hz, 1H), 7.56 (ddd, J=8.5, 4.3, 2.4 Hz, 1H), 7.23 (t, J=9.3 Hz, 1H), 6.62 (s, 2H), 5.31 (t, J=6.9 Hz, 1H), 5.25 (s, 2H), 5.06 (t, J=6.5 Hz, 1H), 3.48 (d, J=7.1 Hz, 2H), 2.15-2.11 (m, 2H), 2.10-2.07 (m, 2H), 1.84 (s, 3H), 1.69 (s, 3H), 1.60 (s, 3H).

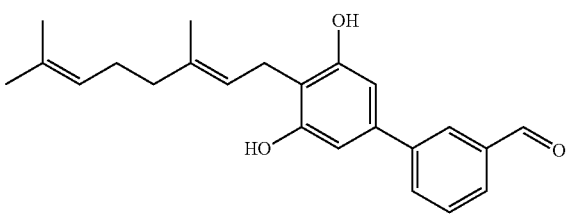 [SMILES: CC(C)=CCC/C(C)=C/Cc1c(O)cc(-c2cccc(C=O)c2)cc1O]

$^1$H NMR (700 MHz, CDCl$_3$) δ 10.07 (s, 1H), 8.05 (s, 1H), 7.84 (d, J=7.5 Hz, 1H), 7.80 (d, J=7.7 Hz, 1H), 7.58 (t, J=7.6 Hz, 1H), 6.70 (s, 2H), 5.31 (t, J=7.2 Hz, 1H), 5.23 (s, 2H), 5.06 (t, J=6.8 Hz, 1H), 3.48 (d, J=7.1 Hz, 2H), 2.13 (q, J=7.2, 6.4 Hz, 2H), 2.11-2.07 (m, 2H), 1.85 (s, 3H), 1.69 (s, 3H), 1.60 (s, 3H).

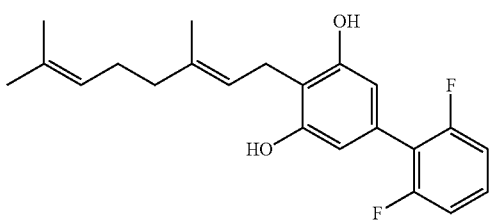

$^1$H NMR (700 MHz, CDCl$_3$) δ 7.28-7.22 (m, 1H), 6.95 (t, J=7.6 Hz, 2H), 6.53 (s, 2H), 5.33 (t, J=7.1 Hz, 1H), 5.07 (t, J=6.7 Hz, 1H), 3.48 (d, J=7.1 Hz, 2H), 2.13 (q, J=7.2 Hz, 2H), 2.09 (d, J=7.2 Hz, 2H), 1.84 (s, 3H), 1.68 (s, 3H), 1.60 (s, 3H).

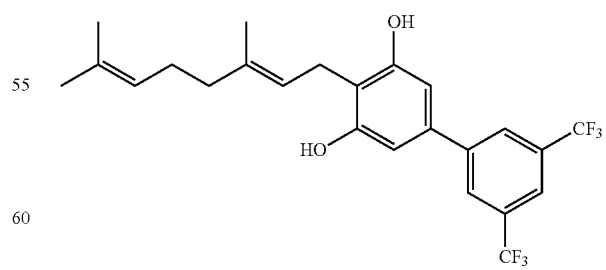

$^1$H NMR (700 MHz, CDCl$_3$) δ 7.95 (s, 2H), 7.81 (s, 1H), 6.67 (s, 2H), 5.30 (t, J=7.0 Hz, 1H), 5.06 (t, J=6.6 Hz, 1H), 3.48 (d, J=7.1 Hz, 2H), 2.13 (q, J=7.2, 6.4 Hz, 2H), 2.10 (d, J=6.9 Hz, 2H), 1.84 (s, 3H), 1.69 (s, 3H), 1.60 (s, 3H).

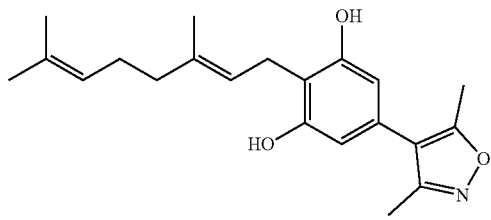 [SMILES: CC(C)=CCC/C(C)=C/Cc1c(O)cc(-c2c(C)noc2C)cc1O]

¹H NMR (700 MHz, CDCl₃) δ 6.31 (s, 2H), 5.75 (s, 2H), 5.31 (t, J=7.0 Hz, 1H), 5.06 (t, J=6.3 Hz, 1H), 3.47 (d, J=7.1 Hz, 2H), 2.39 (s, 3H), 2.26 (s, 3H), 2.13 (q, J=7.2, 6.6 Hz, 2H), 2.10 (d, J=6.9 Hz, 2H), 1.84 (s, 3H), 1.68 (s, 3H), 1.60 (s, 3H).

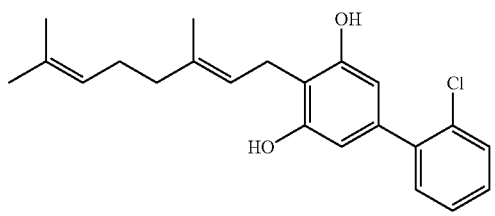 [SMILES: CC(C)=CCC/C(C)=C/Cc1c(O)cc(-c2ccccc2Cl)cc1O]

¹H NMR (700 MHz, CDCl₃) δ 7.40 (d, J=7.6 Hz, 1H), 7.28-7.20 (m, 3H), 6.46 (s, 2H), 5.30 (t, J=6.7 Hz, 1H), 5.18 (s, 2H), 5.03 (t, J=6.1 Hz, 1H), 3.44 (d, J=7.1 Hz, 2H), 2.09 (q, J=7.3, 6.8 Hz, 2H), 2.06 (d, J=7.2 Hz, 2H), 1.80 (s, 3H), 1.65 (s, 3H), 1.57 (s, 3H).

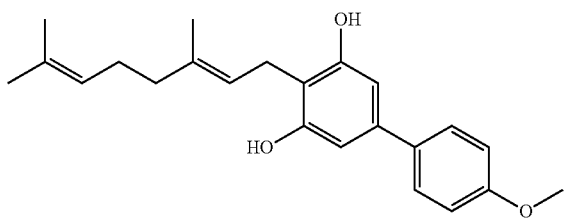 [SMILES: COc1ccc(-c2cc(O)c(C/C=C(\C)CCC=C(C)C)c(O)c2)cc1]

¹H NMR (700 MHz, CDCl₃) δ 7.46 (d, J=8.7 Hz, 2H), 6.93 (d, J=8.7 Hz, 2H), 6.62 (s, 2H), 5.39 (s, 1H), 5.31 (t, J=7.0 Hz, 1H), 5.07 (t, J=6.7 Hz, 1H), 3.84 (s, 3H), 3.46 (d, J=7.1 Hz, 2H), 2.12 (q, J=7.2 Hz, 2H), 2.08 (d, J=7.4 Hz, 2H), 1.84 (s, 3H), 1.69 (s, 3H), 1.60 (s, 3H).

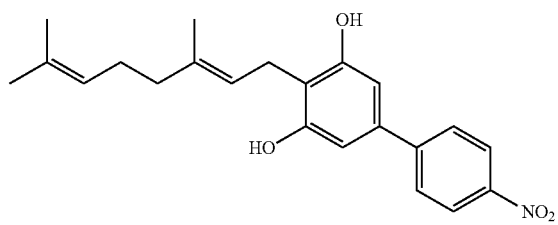 [SMILES: CC(C)=CCC/C(C)=C/Cc1c(O)cc(-c2ccc([N+](=O)[O-])cc2)cc1O]

¹H NMR (700 MHz, CDCl₃) δ 8.25 (d, J=9.0 Hz, 2H), 7.66 (d, J=8.8 Hz, 2H), 6.69 (s, 2H), 5.65 (s, 2H), 5.30 (t, J=7.1 Hz, 1H), 5.06 (t, J=6.5 Hz, 1H), 3.48 (d, J=7.1 Hz, 2H), 2.12 (q, J=6.9 Hz, 2H), 2.10 (t, J=6.7 Hz, 2H), 1.84 (s, 3H), 1.69 (s, 3H), 1.60 (s, 3H).

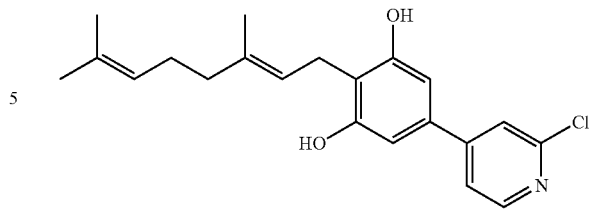

¹H NMR (700 MHz, CDCl₃) δ 8.36 (d, J=4.8 Hz, 1H), 7.65 (d, J=7.5 Hz, 1H), 7.28 (ddd, J=7.4, 4.8, 1.4 Hz, 1H), 6.51 (s, 2H), 5.58 (s, 2H), 5.33 (t, J=7.3 Hz, 1H), 5.07 (t, J=6.4 Hz, 1H), 3.49 (d, J=7.1 Hz, 2H), 2.13 (q, J=7.2, 6.6 Hz, 2H), 2.11-2.08 (m, 2H), 1.84 (s, 3H), 1.68 (s, 3H), 1.60 (s, 3H).

Example 2: Evaluation of Minimal Inhibitory Concentration (MIC) for Compounds of the Invention The protocol for MIC determination is based on the Clinical & Laboratory Standards Institute (CLSI) guidelines. MICs are determined by setting up 96-well microtiter plates with serially diluted concentrations in DMSO or water ranging from 0-256 μg/mL for each compound of the invention (e.g., 256 μg/mL, 128 μg/mL, 64 μg/mL, 32 μg/mL, 16 μg/mL, 8 μg/mL, 4 μg/mL, 2 μg/mL, 1 μg/mL, etc.). The total volume in each plate is about 200 μL, with 2 μL of each serial dilution added to each well. Clinical isolates of various bacteria are obtained from the American Type Culture Collection (ATCC) and colony-resuspended for MIC testing as per CLSI guidelines. Plates are incubated at 37° C. for 18 hours, and optical density is read on a Tecan M1000 Infinite Pro plate reader at 600 nm. At least 3 replicates are done for each query compound. The MIC for each compound is the lowest compound concentration showing <10% bacterial growth.

Example 3: Evaluation of Antibacterial Activity of the Compounds of the Invention in the Presence of Another Antibacterial Agent The effect of another antibacterial agent on the activity of the compounds of the invention is evaluated. Clinical isolates of various bacteria are obtained from the American Type Culture Collection (ATCC) and the International Health Management Associates (IHMA). Fractional inhibitory concentration indices (FICIs) are determined by setting up standard checkerboard broth microdilution assays in 96-well microtiter plates with serially diluted 8 (or 10) concentrations of each drug (disclosed compounds and the other antibacterial agent). The protocol for checkerboard analyses is based on the Clinical & Laboratory Standards Institute (CLSI) guidelines. Plates are incubated at 37° C. for 18 hours, and optical density is read on a Tecan M1000 Infinite Pro plate reader at 600 nm. At least 3 replicates are performed for each query compound.

This protocol was used to determine the FICIs for the following sample compounds when combined with Colistin against E. coli. The sample compounds were used at concentrations ranging from 0-32 μg/mL and Colistin was used at concentrations ranging from 0-0.5 μg/mL.

The results confirm the efficacy of both compositions to inhibit growth of the gram negative bacterium, *E. coli*. The checkerboards shown in FIG. 1 both display synergy (which requires a FICI < or equal to 0.5). Compound MLEB-1917 has a FICI of <0.375 and Compound MLEB-1850 has a FICI of <0.5.

Example 4—Efficacy of Compounds of Formula (1)

The protocol as described in Example 2 was used to determine the minimal inhibitory concentration (MIC) of each of the following compounds against a strain of *S. aureus* and Pore-TolC *E. coli*.

TABLE 2

| Compound ID | Structure | Staph MIC (mg/L) | Pore-TolC E. coli MIC (ug/mL) |
| --- | --- | --- | --- |
| MLEB-19121 | 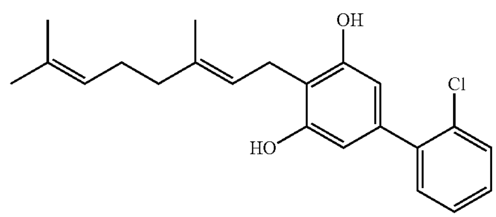 [SMILES: CC(C)=CCC/C(C)=C/Cc1c(O)cc(-c2ccccc2Cl)cc1O] | 0.5 | ND |
| MLEB-19114 | 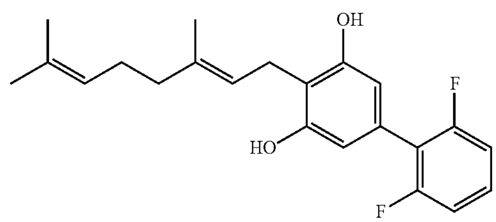 [SMILES: CC(C)=CCC/C(C)=C/Cc1c(O)cc(-c2c(F)cccc2F)cc1O] | 1 | 0.5 |
| MLEB-19118 | 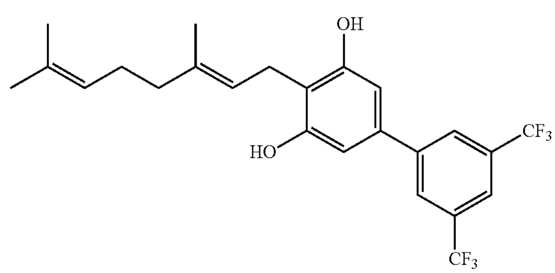 [SMILES: CC(C)=CCC/C(C)=C/Cc1c(O)cc(-c2cc(C(F)(F)F)cc(C(F)(F)F)c2)cc1O] | 1 | 8 |
| MLEB-1999 | 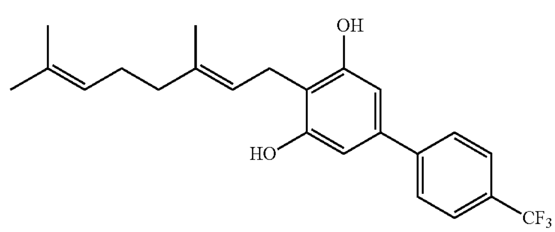 [SMILES: CC(C)=CCC/C(C)=C/Cc1c(O)cc(-c2ccc(C(F)(F)F)cc2)cc1O] | 1 | 2 |
| MLEB-19112 | 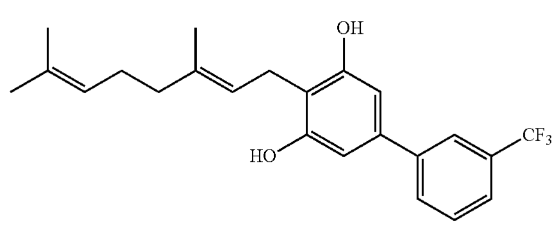 [SMILES: CC(C)=CCC/C(C)=C/Cc1c(O)cc(-c2cccc(C(F)(F)F)c2)cc1O] | 1 | 1 |

TABLE 2-continued
| Compound ID | Structure | Staph MIC (mg/L) | Pore-TolC E. coli MIC (ug/mL) |
|---|---|---|---|
| MLEB-19132 | 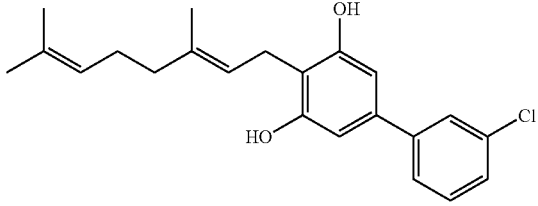 | 1 | 1 |
| MLEB-19137 | 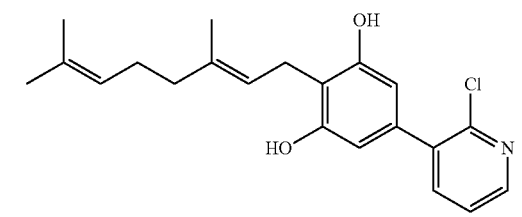 [SMILES: CC(C)=CCC/C(C)=C/Cc1c(O)cc(-c2cccnc2Cl)cc1O] | 1 | 1 |
| MLEB-19134 | 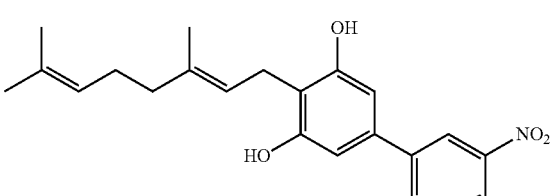 | 1 | 1 |
| MLEB-19102 | 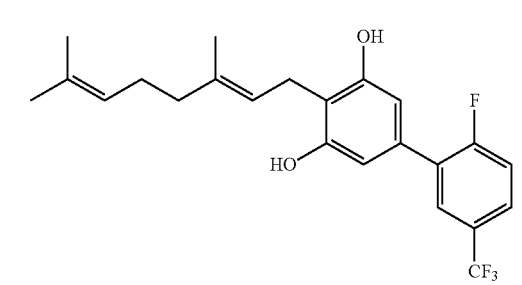 | 2 | 2 |
| MLEB-19101 | 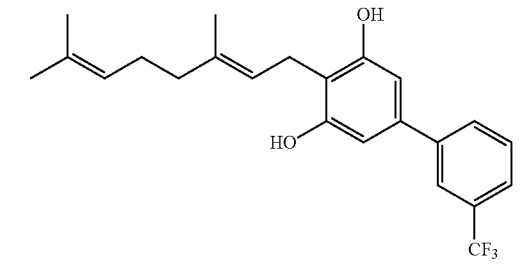 [SMILES: CC(C)=CCC/C(C)=C/Cc1c(O)cc(-c2cccc(C(F)(F)F)c2)cc1O] | 2 | 1 |
| MLEB-19100 | 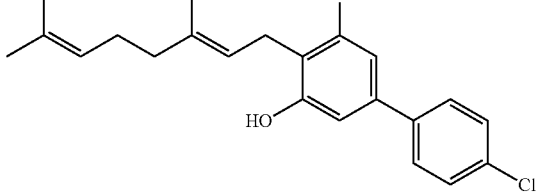 | 2 | 2 |

TABLE 2-continued

| Compound ID | Structure | Staph MIC (mg/L) | Pore-TolC E. coli MIC (ug/mL) |
| --- | --- | --- | --- |
| MLEB-1997 | 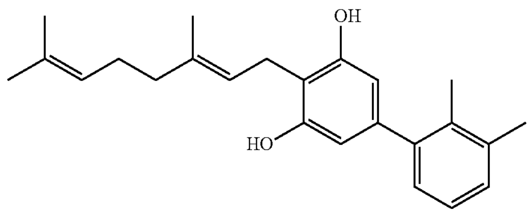 [SMILES: CC(C)=CCC/C(C)=C/Cc1c(O)cc(-c2cccc(C)c2C)cc1O] | 2 | 1 |
| MLEB-19130 | 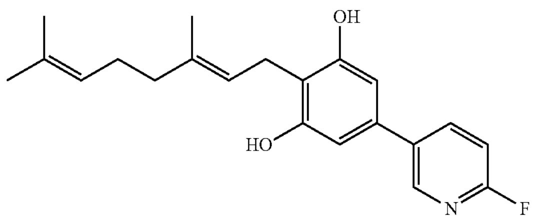 [SMILES: CC(C)=CCC/C(C)=C/Cc1c(O)cc(-c2ccc(F)nc2)cc1O] | 2 | 2 |
| MLEB-19131 | 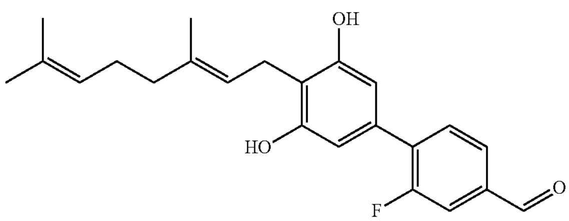 [SMILES: CC(C)=CCC/C(C)=C/Cc1c(O)cc(-c2ccc(C=O)cc2F)cc1O] | 2 | 2 |
| MLEB-19164 | 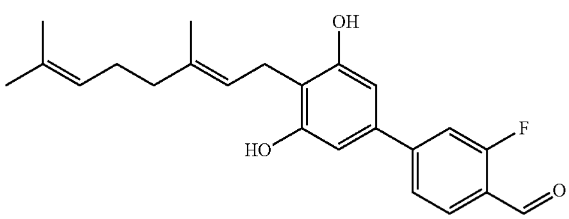 [SMILES: CC(C)=CCC/C(C)=C/Cc1c(O)cc(-c2ccc(C=O)c(F)c2)cc1O] | 2 | 4 |
| MLEB-19120 | 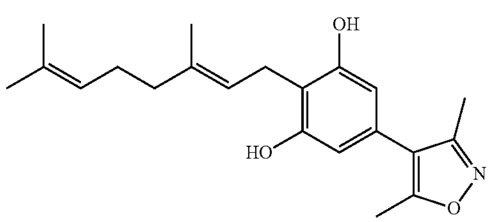 [SMILES: CC(C)=CCC/C(C)=C/Cc1c(O)cc(-c2c(C)noc2C)cc1O] | 2 | ND |
| MLEB-19165 | 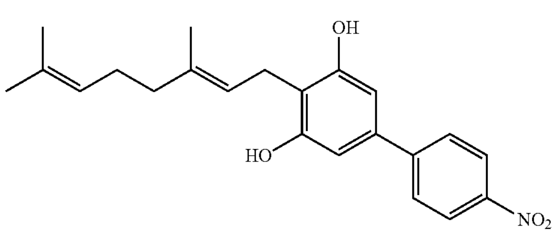 [SMILES: CC(C)=CCC/C(C)=C/Cc1c(O)cc(-c2ccc([N+](=O)[O-])cc2)cc1O] | 2 | 1 |
| MLEB-19162 | 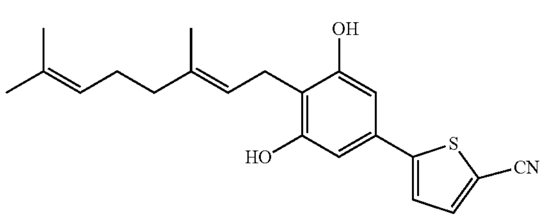 [SMILES: CC(C)=CCC/C(C)=C/Cc1c(O)cc(-c2ccc(C#N)s2)cc1O] | 2 | 4 |

TABLE 2-continued

| Compound ID | Structure | Staph MIC (mg/L) | Pore-TolC E. coli MIC (ug/mL) |
|---|---|---|---|
| MLEB-1917 | 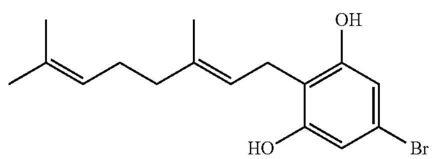 [SMILES: CC(C)=CCC/C(C)=C/Cc1c(O)cc(Br)cc1O] | 4 | 0.5 |
| MLEB-1998 | 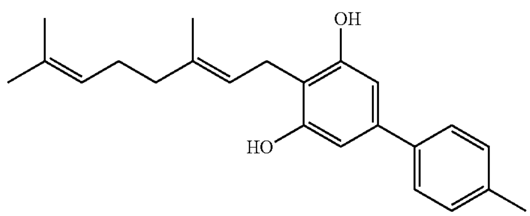 [SMILES: CC(C)=CCC/C(C)=C/Cc1c(O)cc(-c2ccc(C)cc2)cc1O] | 4 | 1 |
| MLEB-1864 | 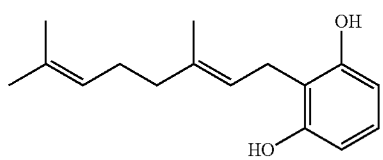 [SMILES: CC(C)=CCC/C(C)=C/Cc1c(O)cccc1O] | 4 | 1 |
| MLEB-19163 | 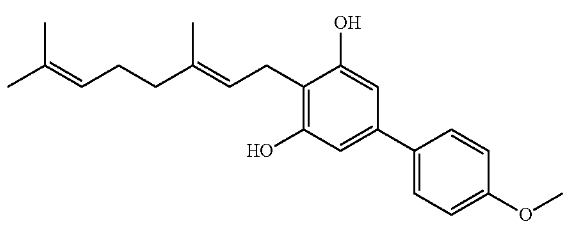 | 4 | 2 |
| MLEB-19135 | 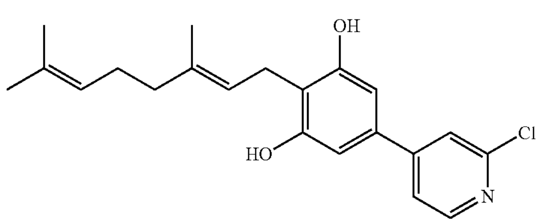 [SMILES: CC(C)=CCC/C(C)=C/Cc1c(O)cc(-c2ccnc(Cl)c2)cc1O] | 4 | 1 |
| MLEB-19133 | 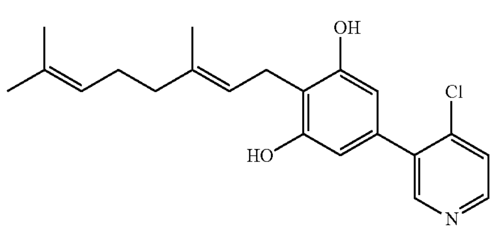 [SMILES: CC(C)=CCC/C(C)=C/Cc1c(O)cc(-c2cnccc2Cl)cc1O] | 4 | 2 |
| MLEB-19128 | 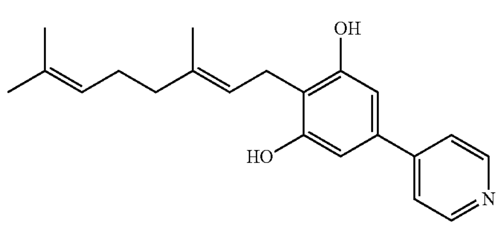 [SMILES: CC(C)=CCC/C(C)=C/Cc1c(O)cc(-c2ccncc2)cc1O] | 4 | 2 |

TABLE 2-continued

| Compound ID | Structure | Staph MIC (mg/L) | Pore-TolC E. coli MIC (ug/mL) |
|---|---|---|---|
| MLEB-19115 | 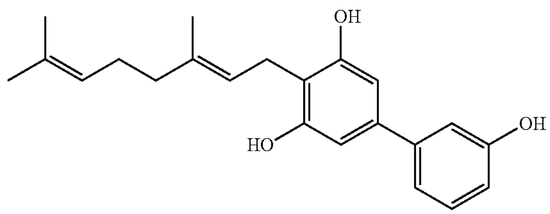 [SMILES: CC(C)=CCC/C(C)=C/Cc1c(O)cc(-c2cccc(O)c2)cc1O] | 4 | 2 |
| MLEB-19136 | 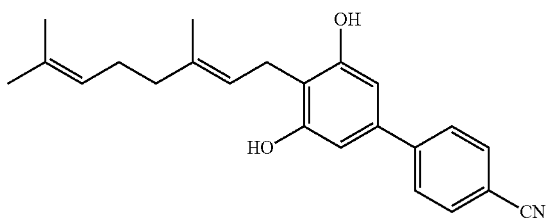 [SMILES: CC(C)=CCC/C(C)=C/Cc1c(O)cc(-c2ccc(C#N)cc2)cc1O] | 4 | 2 |
| MLEB-19161 | 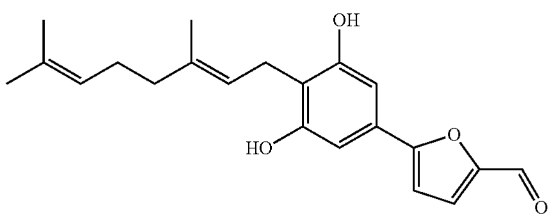 [SMILES: CC(C)=CCC/C(C)=C/Cc1c(O)cc(-c2ccc(C=O)o2)cc1O] | 4 | 4 |
| MLEB-19117 | 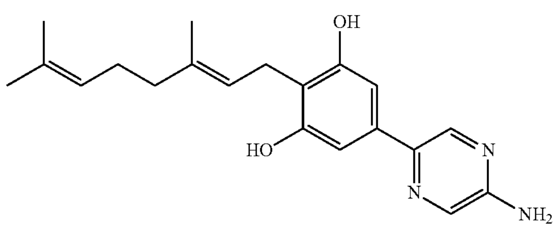 [SMILES: CC(C)=CCC/C(C)=C/Cc1c(O)cc(-c2cnc(N)cn2)cc1O] | 4 | ND |
| MLAP-1913 | 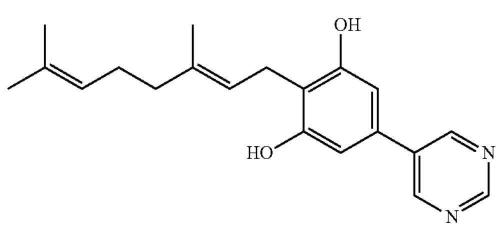 [SMILES: CC(C)=CCC/C(C)=C/Cc1c(O)cc(-c2cncnc2)cc1O] | 8 | 2 |
| MLEB-1850 | 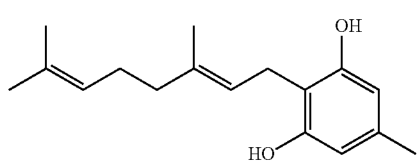 [SMILES: CC(C)=CCC/C(C)=C/Cc1c(O)cc(C)cc1O] | 8 | 2 |
| MLEB-19110 | 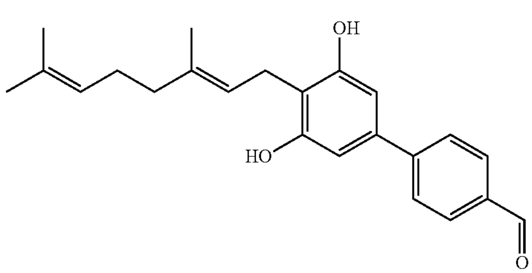 [SMILES: CC(C)=CCC/C(C)=C/Cc1c(O)cc(-c2ccc(C=O)cc2)cc1O] | 8 | ND |

TABLE 2-continued
| Compound ID | Structure | Staph MIC (mg/L) | Pore-TolC E. coli MIC (ug/mL) |
|---|---|---|---|
| MLEB-19108 | 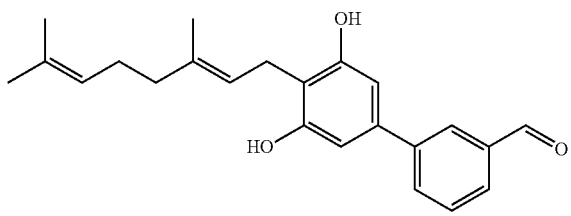 [SMILES: CC(C)=CCC/C(C)=C/Cc1c(O)cc(-c2cccc(C=O)c2)cc1O] | 8 | ND |
| MLEB-19116 | 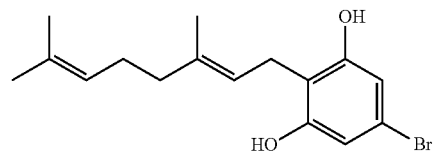 [SMILES: CC(C)=CCC/C(C)=C/Cc1c(O)cc(Br)cc1O] | 8 | 4 |
| MLEB-19138 | 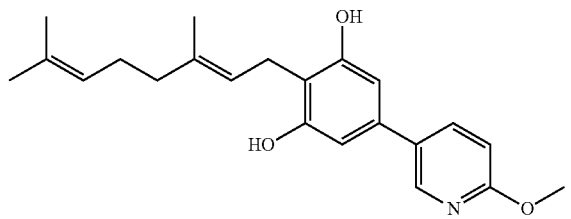 [SMILES: COc1ccc(-c2cc(O)c(C/C=C(\C)CCC=C(C)C)c(O)c2)cn1] | 16 | ND |
| MLEB-19139 | 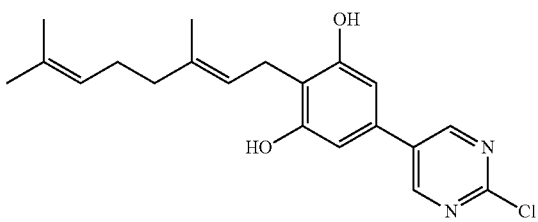 [SMILES: CC(C)=CCC/C(C)=C/Cc1c(O)cc(-c2cnc(Cl)nc2)cc1O] | 16 | 4 |
| MLEB-19129 | 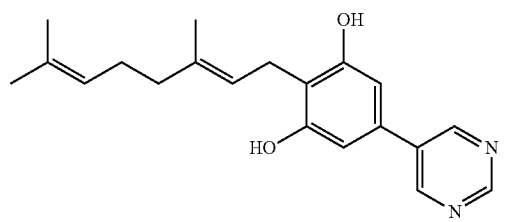 [SMILES: CC(C)=CCC/C(C)=C/Cc1c(O)cc(-c2cncnc2)cc1O] | 16 | 8 |
| MLEB-19109 | 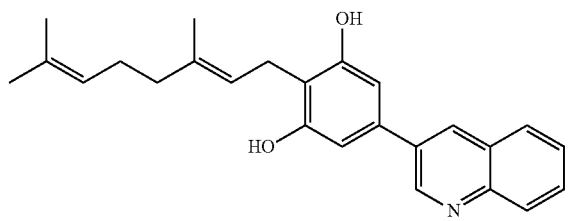 [SMILES: CC(C)=CCC/C(C)=C/Cc1c(O)cc(-c2cnc3ccccc3c2)cc1O] | 32 | 32 |

TABLE 2-continued

| Compound ID | Structure | Staph MIC (mg/L) | Pore-TolC E. coli MIC (ug/mL) |
|---|---|---|---|
| MLEB-1996 | 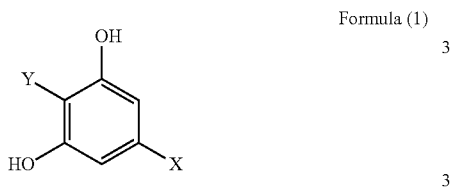 | 32 | >32 |

All publications, patents and patent applications are herein incorporated by reference in their entirety to the same extent as if each individual publication, patent or patent application was specifically and individually indicated to be incorporated by reference in its entirety.

The invention claimed is:

1. A compound having the structure of formula (1),

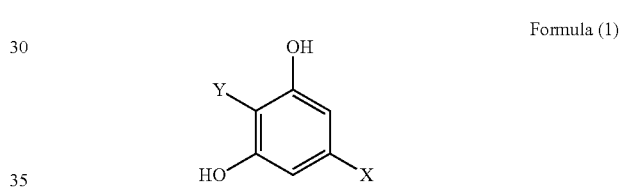

Formula (1)

wherein X is a substituted or unsubstituted aromatic or heteroaromatic mono- or polycyclic ring system; and
Y is a 2,6-octadienyl group comprising one or more alkyl branches,
or a pharmaceutically acceptable salt thereof,
with the proviso that the compound is not 2-[3,5-dihydroxy-4-(3,7-dimethyl-2,6-octadienyl)phenyl]-6-hydroxybenzofuran.

2. The compound of claim 1, wherein X is a mono- or bi-cyclic aromatic or heteroaromatic ring.

3. The compound[s] of claim 1, wherein X is an aromatic mono-cyclic ring selected from a phenyl ring, furan, thiophene, pyrrole, pyrazole, pyridine, pyrimidine, pyrazine, pyridazine, thiazole, oxazole, isoxazole and thiazopine.

4. The compound of claim 1, wherein X is substituted with a substituent selected from the group consisting of hydroxyl, halogen, alkyl, amino, nitro, nitrile, carboxyl, thiol, sulfinyl, sulfonamide and sulfinamide.

5. The compound of claim 1, wherein X is substituted with a substituent selected from the group consisting of alkyl, alkenyl, alkoxy, alkanal, alkanone, acetyl, alkoxycarbonyl, amine, amide, sulfoxide or sulfonyl, optionally substituted with one or more groups selected from the group consisting of hydroxyl, halogen, alkyl, amino, nitro, nitrile, carboxyl, thiol, sulfinyl, sulfonamide and sulfinamide.

6. The compound of claim 1, wherein Y is 3,7-dimethyl-2,6-octa-dienyl.

7. A composition comprising (i) an effective amount of the compound or pharmaceutically acceptable salt of the compound of claim 1 and (ii) a pharmaceutically acceptable carrier or vehicle.

8. The composition of claim 7, wherein the composition further comprises another antibacterial agent.

9. A method for inhibiting growth of a bacterium, comprising contacting the bacterium with a compound having the structure of formula (1), Formula (1)

wherein X is a substituted or unsubstituted aromatic or heteroaromatic mono- or polycyclic ring system; and
Y is a 2,6-octadienyl group comprising one or more alkyl branches,
or a pharmaceutically acceptable salt thereof.

10. The method of claim 9, wherein X in the compound is a mono- or bi- cyclic aromatic or heteroaromatic ring.

11. The method of claim 9, wherein X in the compound is an aromatic mono-cyclic ring selected from a phenyl ring, furan, thiophene, pyrrole, pyrazole, pyridine, pyrimidine, pyrazine, pyridazine, thiazole, oxazole, isoxazole and thiazopine.

12. The method of claim 9, wherein Y in the compound is 3,7-dimethyl-2,6-octa-dienyl.

13. The method of claim 9, further comprising contacting the bacterium with another antibacterial agent.

14. The compound of claim 1, wherein X is a mono- or bi-cyclic aromatic or heteroaromatic ring.

15. The compound of claim 14, wherein X is substituted with a substituent selected from the group consisting of hydroxyl, halogen, alkyl, alkoxy, alkanal, alkanone, acetyl, amine, amino, amide, nitro, nitrile, carboxyl, cyano, thiol, sulfinyl and sulfoxide.

16. The compound of claim 15, wherein X is a monocyclic aromatic or heteroaromatic ring.

17. The compound of claim 16, wherein X is phenyl.

* * * * *